United States Patent [19]

Nagamine et al.

[11] Patent Number: 5,464,863
[45] Date of Patent: Nov. 7, 1995

[54] N-HETEROARYL-N'-PHENYLUREA DERIVATIVES, THEIR PRODUCTION AND USE

[75] Inventors: Masashi Nagamine, Gose; Kenji Yamamoto; Yoshimitsu Matsui, both of Kawachinagano; Kenji Horiuchi, Daito; Masanori Yoshida, Hashimoto, all of Japan

[73] Assignee: Nihon Nohyaku Co., Ltd., Japan

[21] Appl. No.: 201,378

[22] Filed: Sep. 24, 1994

[30] Foreign Application Priority Data

Feb. 27, 1993 [JP] Japan .................................. 5-063460

[51] Int. Cl.$^6$ .......................... A61K 31/38; C07D 333/66
[52] U.S. Cl. ........................ 514/443; 549/57; 549/58
[58] Field of Search ........................ 549/31, 32, 57, 549/58; 514/443

[56] References Cited

U.S. PATENT DOCUMENTS

| 4,113,731 | 9/1978 | Winters et al. ............... 260/288 |
| 4,157,399 | 6/1979 | Sauter ........................... 424/275 |

FOREIGN PATENT DOCUMENTS

| 0399422 | 11/1990 | European Pat. Off. . |
| 0506532 | 9/1992 | European Pat. Off. . |
| 0512570 | 11/1992 | European Pat. Off. . |
| 10602598 | 6/1994 | European Pat. Off. . |
| 3-7259 | 1/1991 | Japan . |
| 3-223254 | 10/1991 | Japan . |

OTHER PUBLICATIONS

Farmaco, Edizione Scientifica, vol. 34, 1979, Pavia It, pp. 507–517, G. Winters et al. 'Synthesis and Biological Activities of Some Indolo[2,3–c]isoquinoline Derivatives' p. 516, paragraph 2, table II.
Chemical Abstract vol. 90, 87163k (1978).
Chemical Abstract vol. 91, 175235m (1979).

Primary Examiner—Richard L. Raymond
Assistant Examiner—Mary C. Cebulak
Attorney, Agent, or Firm—Cushman Darby & Cushman

[57] ABSTRACT

An N-heteroaryl-N'-phenylurea derivative represented by the general formula (I):

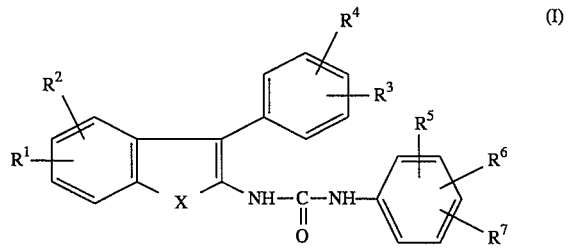

wherein $R^1$, $R^2$, $R^3$, $R^4$, $R^5$, $R^6$ and $R^7$ are as defined in the description of the specification which is useful as a prophylactic and therapeutic agent for hypercholesterolemia, atherosclerosis and diseases caused by them.

6 Claims, No Drawings

N-HETEROARYL-N'-PHENYLUREA DERIVATIVES, THEIR PRODUCTION AND USE

BACKGROUND OF THE INVENTION

1. Field of the Invention

The present invention relates to N-heteroaryl-N'-phenylurea derivatives or pharmacologically acceptable salts thereof, which have inhibitory effect on acyl-CoA:cholesterol O-acyltransferase (ACAT).

The compounds of the present invention have the effect of reducing serum cholesterol by inhibiting the absorption of cholesterol from intestinal tract and suppress the accumulation of cholesterol esters in the arterial wall. Therefore, they are useful as a prophylactic and therapeutic agent for hypercholesterolemia, atherosclerosis and various diseases caused by them (for example, ischemic heart diseases such as myocardial infarction, and cerebrovascular diseases such as cerebral infarction and cerebral apoplexy).

2. Related Art

As to N-heteroaryl-N'-phenylurea derivatives, there are the following disclosures.

Japanese Patent Unexamined Publication No. 3-7259 discloses that N-quinoline-N'-phenylurea derivatives represented by the formula (A):

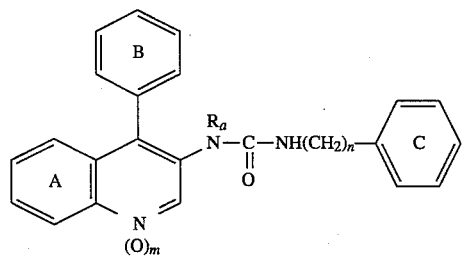

(wherein the ring A, ring B and ring C may have a substituent, and each of m and n is zero or an integer of 1) have ACAT-inhibitory activity. Japanese Patent Unexamined Publication No. 3-223254 discloses that N-quinoline-N'-phenylurea derivatives represented by the formula (B):

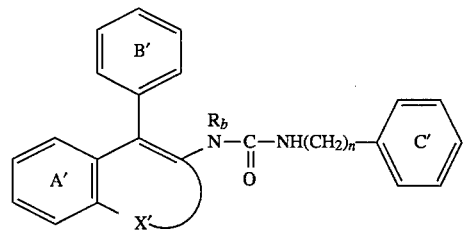

(wherein the ring A', ring B and ring C' may have a substituent, n is zero or an integer of 1, and X' is

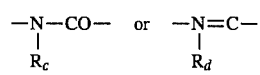

have ACAT-inhibitory activity.

J. Ind. Chem. Soc., 1978, 55(9), 910–913 discloses that compounds having, like the compounds of the present invention, a benzofuran skeleton which are represented by the formula (C):

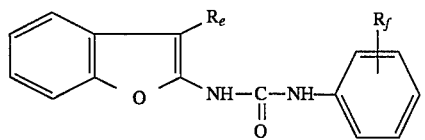

(wherein Re is a hydrogen atom or a methyl group) have antimicrobial activity, antibacterial activity, antiparasitic activity and anti-amoeba activity.

Farmaco, Ed. Sci. 1979, 34(6), 507–517 describes compounds having an indole skeleton which are represented by the formula (D):

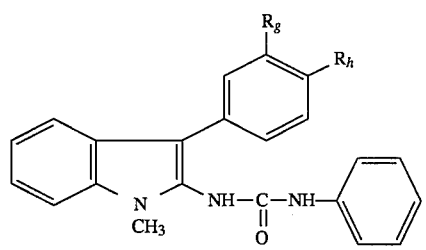

but it does not describes them as having ACAT-inhibitory activity.

OBJECT AND SUMMARY OF THE INVENTION

The present inventors investigated N-heteroaryl derivatives and consequently found that a compound represented by the general formula (I):

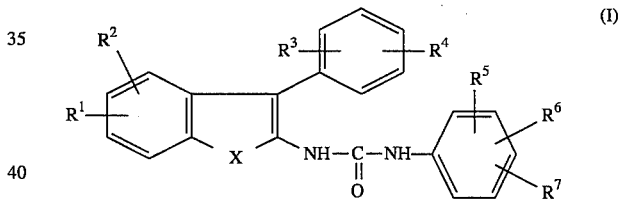

wherein $R^1$ and $R^2$, which may be the same or different, are hydrogen atoms; halogen atoms; unsubstituted $C_1$–$C_{10}$ alkyl groups; substituted $C_1$–$C_6$ alkyl groups having a $C_2$–$C_8$-dialkylamino group as the substituent; substituted lower alkyl groups having as the substituent a saturated cyclic amino group which may have a heteroatom in the ring; $C_1$–$C_6$ alkoxy groups; or nitro groups, $R^1$ and $R^2$ being able to be taken together to represent a $C_3$–$C_6$ alkylene group, $R^3$ and $R^4$, which may be the same or different, are hydrogen atoms, halogen atoms, $C_1$–$C_6$ alkyl groups, $C_1$–$C_6$ haloalkyl groups, $C_1$–$C_6$ alkoxy groups or $C_1$–$C_6$ alkylthio groups, $R^5$, $R^6$ and $R^7$, which may be the same or different, are hydrogen atoms, halogen atoms, $C_1$–$C_8$ alkyl groups, $C_1$–$C_6$ haloalkyl groups, $C_3$–$C_7$ alkenyl groups, $C_1$–$C_6$ alkoxy groups, $C_1$–$C_6$ alkylthio groups or $C_2$–$C_8$-dialkylamino groups, and X is —O—, —S— or —NR— (wherein R is a $C_1$–$C_6$ alkyl group, a phenylsulfonyl group or a toluenesulfonyl group) or a pharmacologically acceptable salt thereof is a novel compound not known in any literature and has an excellent ACAT-inhibiting activity, whereby the present invention has been accomplished.

An object of the present invention is to provide novel N-heteroaryl-N'-phenylurea derivatives having an excellent ACAT inhibitory activity.

An another object of the present invention is to provide a pharmaceutical composition useful as a prophylactic and therapeutic agent for hypercholesterolemia, arteriosclerosis and diseases caused by them.

An further another object of the present invention is to provide a method of preparing N-heteroaryl-N'-phenylurea derivatives.

DETAILED DESCRIPTION OF THE PREFERRED EMBODIMENTS

In the above general formula (I), the halogen atoms include fluorine atom, chlorine atom, bromine atom and iodine atom. The lower alkyl groups include linear or branched alkyl groups having 1 to 6 carbon atoms, such as methyl, ethyl, n-propyl, isopropyl, n-butyl, isobutyl, sec-butyl, tert-butyl, n-pentyl, isopentyl, neopentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 2-ethylbutyl, 1,1,2-trimethylpropyl, 1,2,2-trimethylpropyl, 1-ethyl-1-methylpropyl and the like. The lower haloalkyl groups include trichloromethyl group, trifluoromethyl group, 1,1,1-trifluoroethyl group, etc. The lower alkoxy groups include methoxy group, ethoxy group, n-propoxy group, isopropoxy group, n-butoxy group, isobutoxy group, sec-butoxy group, tert-butoxy group, etc. The lower alkylthio groups include methylthio group, ethylthio group, n-propylthio group, isopropylthio group, n-butylthio group, isobutylthio group, sec-butylthio group, tert-butylthio group, etc.

Preferable N-heteroaryl-N'-phenylurea derivatives are those whose $R^1$ is a halogen atom or a $C_1$–$C_{10}$ alkyl group, $R^2$ is a hydrogen atom or a $C_1$–$C_6$ alkyl group, $R^1$ and $R^2$ being able to be taken together to represent a $C_3$–$C_6$ alkylene group, $R^3$ is a halogen atom, a $C_1$–$C_4$ alkyl group, a $C_1$–$C_4$ alkylthio group or trifluoromethyl group, $R^4$ is a hydrogen atom or a halogen atom, $R^5$ and $R^6$ which may be the same or different, are halogen atoms or $C_1$–$C_4$ alkyl groups, and $R^7$ is a hydrogen atom or a halogen atom.

More preferable N-heteroaryl-N'-phenylurea derivatives are those whose $R^1$ is a chlorine atom or a $C_1$–$C_8$ alkyl group, $R^2$ is a halogen atom or a $C_1$–$C_3$ alkyl group, $R^1$ and $R^2$ being able to be taken together to represent a $C_3$–$C_4$ alkylene group, $R^3$ is a halogen atom, a $C_1$–$C_4$ alkyl group or a $C_1$–$C_4$ alkylthio group, $R^4$ is a hydrogen atom, $R^5$ and $R^6$ which may be the same, are halogen atoms or $C_1$–$C_4$ alkyl groups, and $R^7$ is a hydrogen atom.

Of the compound of the present invention, those which are particularly useful as an ACAT inhibitor will be shown bellow:

N-[5-chloro-3-(2-chlorophenyl)benzofuran-2-yl]-N'-(2,6-diethylphenyl)urea,

N-[5-chloro-3-(2-chlorophenyl)benzofuran-2-yl]-N'-(2,6-diisopropylphenyl)urea,

N-[3-(2-chlorophenyl)-5-hexylbenzofuran-2-yl]-N'-(2,6-diisopropylphenyl)urea,

N-[3-(2-chlorophenyl)-5,7-dimethylbenzofuran-2-yl]-N'-(2,6-diisopropylphenyl)urea, N-[5-chloro-3-(2-methylphenyl)benzofuran-2-yl]-N'-(2,6-diethylphenyl)urea, N-(3-(2-chlorophenyl)-5-iospropyl-1-benzothiophen-2-yl]-N'-(2,6-diethylphenyl)urea, N-[3-(2-chlorophenyl)-5-isopropyl-1-benzothiophen-2-yl]-N''-2,6-diisopropylphenyl)urea, N-[3-(2-chlorophenyl)-5,6-dimethyl-1-benzothiohen-2-yl]-N'-(2,6-diethylphenyl)urea, N-2,6-diethylphenyl)-N'-[3-(2-methylphenyl)-6,7-dihydro-5H-cyclopenta[f][1]-benzothiophen-2-yl]urea, N-3-(2-chlorophenyl)-5-fluorobenzofuran-2-yl]-N'-(2,6-diethylphenyl)urea, N-[5-chloro-3-(2-chlorophenyl)benzofuran-2-yl]-N'-(2,6-dimethylamino-6-methylphenyl)urea, N-[3-(2-chlorophenyl)-5-ethylbenzofuran-2-yl]-N'-(2,6-diisopropylphenyl)urea, N-[3-(2-chlorophenyl)-5,6-dimethylbenzofuran-2-yl]-N'-(2,6-diethylphenyl)urea, N-[5-chloro-3-(2-methylthiophenyl)benzofuran-2-yl]-N'-(2,6-diethylphenyl)urea, N-[5-chloro-3-(2-chlorophenyl)-1-benzothiophen-2-yl]-N'-(2,6-diethylphenyl)urea, N-[3-(2-chlorophenyl)-6,7-dihydro-5H-cyclopenta[f][1]benzothiophen-2-yl]-N'-(2,4-difluorophenyl)urea, N-[3-(2-chlorophenyl)-6,7-dihydro-5H-cyclopenta[f][1]benzothiophen-2-yl]-N'-(2,4,6-trifluorophenyl)urea, N-[3-(2-chlorophenyl)-5,6,7,8-tetrahydronaphtho[2,3-b]thiophen-2-yl]-N'-(2-isopropyl-6-methylphenyl)urea, and N-(2-isopropyl-6-methylphenyl)-N'-[3-(2-methylphenyl)-6,7-dihydro-5H-cyclopenta[f][1]benzothiophen-2-yl]urea.

The compound of the general formula (I) can be synthesized by a process represented by the following formulas:

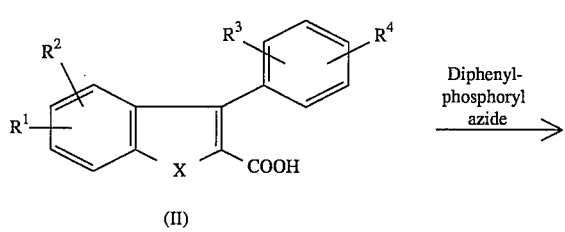

(II)

Diphenylphosphoryl azide →

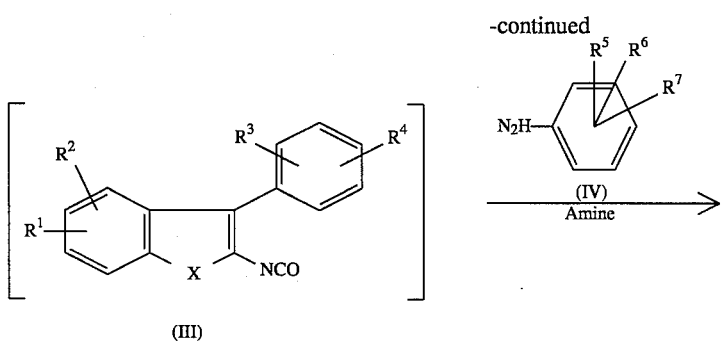

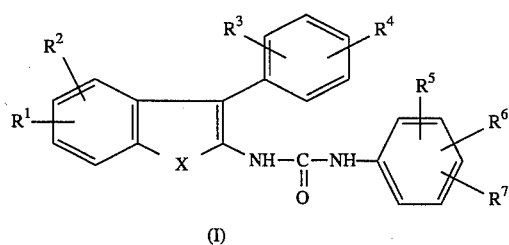

wherein $R^1$, $R^2$, $R^3$, $R^4$, $R^5$, $R^6$, $R^7$ and X are as defined above.

In detail, the compound of the general formula (I) can be produced by reacting a compound of the general formula (II) with diphenylphosphoryl azide in the presence of an organic amine such as triethylamine in an inert solvent such as benzene, toluene, xylene or dioxane in a temperature range of room temperature to about 150° C. to obtain an isocyanate (III), and then reacting the isocyanate with a compound of the general formula (IV) in a temperature range of room temperature to about 150° C. after or without isolating the isocyanate. Since the reactions are equimolar reactions, it is sufficient that the reactants for carrying out each reaction are used in equimolar amounts, though either of them may be used in excess.

The compound of the general formula (II) used in the reaction can be synthesized by any of the following processes.

Process A (in the case where X=O)

The compound of the general formula (II) can be synthesized from a compound of the formula (V) by the process described in J. Ind. Chem. Soc. 33, 339 (1956) and Brit. 705,950 or a process based thereon.

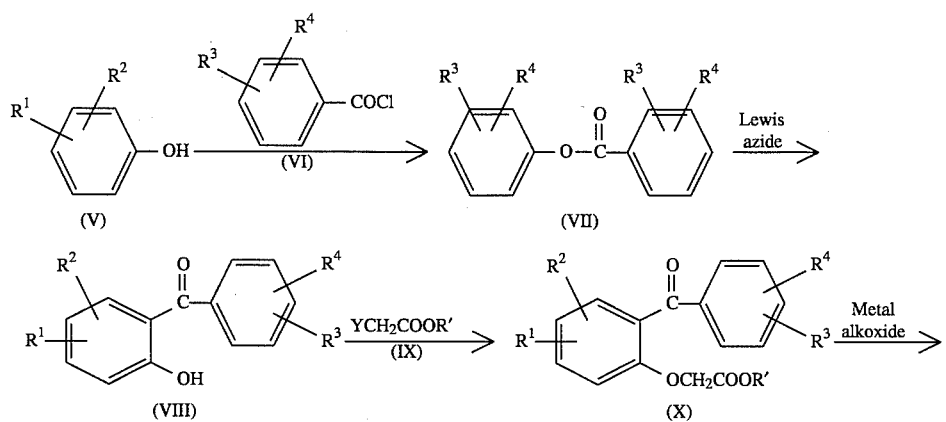

-continued

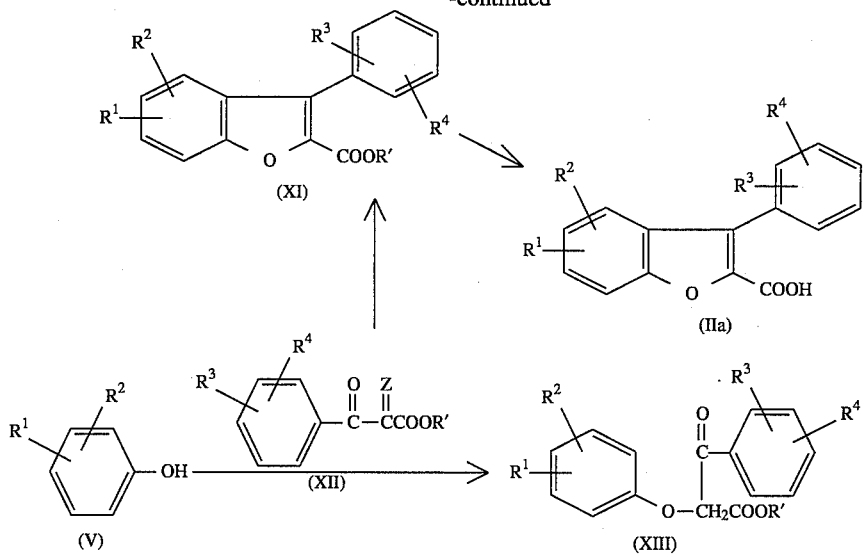

wherein $R^1$, $R^2$, $R^3$ and $R^4$ are as defined above, R' is a lower alkyl group, Y is a halogen atom such as a chlorine atom or bromine atom, and Z is a diazo group.

In detail, a phenol (V) is benzoylated into a compound (VII) by a conventional method, and the compound (VII) is heated in the presence of a Lewis acid (e.g. aluminum chloride, aluminum bromide or titanium tetrabromide) to obtain a hydroxybenzophenone (VIII). This reaction can be carried out in an inert solvent such as carbon disulfide or nitrobenzene or without a solvent in a temperature range of room temperature to about 180° C. Then, the compound (VIII) is reacted with a compound (IX) in the presence of an inorganic base (e.g. potassium carbonate, sodium carbonate or lithium carbonate) in a solvent (e.g. dimethylformamide, dimethyl sulfoxide, acetonitrile or acetone) in a temperature range of room temperature to about 100° C. to obtain a compound (X). Next, the compound (X) is subjected to ring-closing reaction with a metal alkoxide (e.g. sodium methoxide, sodium ethoxide, sodium isopropoxide or potassium t-butoxide) in a solvent (e.g. methanol, ethanol, isopropanol, t-butanol, tetrahydrofuran or dioxane) in a temperature range of room temperature to about 80° C. to obtain a benzofuran (XI). Subsequently, the compound (XI) is hydrolyzed with an aqueous alkali metal hydroxide solution such as sodium hydroxide or potassium hydroxide, trifluoroacetic acid, or a mineral acid (e.g. hydrochloric acid, sulfuricacid or hydrobromic acid) in a solvent (e.g. methanol, ethanol, isopropanol or dioxane) in a temperature range of room temperature to about 120° C. to obtain a compound (IIa).

The compound of the formula (XI) can be obtained also by reacting an α-diazobenzoylacetic acid ester (XII) with a phenol (V) in the presence of a rhodium(II) carboxylate catalyst such as rhodium(II) acetate in a solvent such as carbon tetrachloride or acetonitrile in a temperature range of room temperature to about 50° C. to obtain a compound (XIII), and then reacting the compound (XIII) with sulfuric acid in a temperature range of approximately 0°–10° C.

Process B (in the case where X=S)

The compound of the general formula (II) can be synthesized from a compound of the formula (XIV) by the process described in J. Org. Chem. 23, 206 (1958) or a process based thereon.

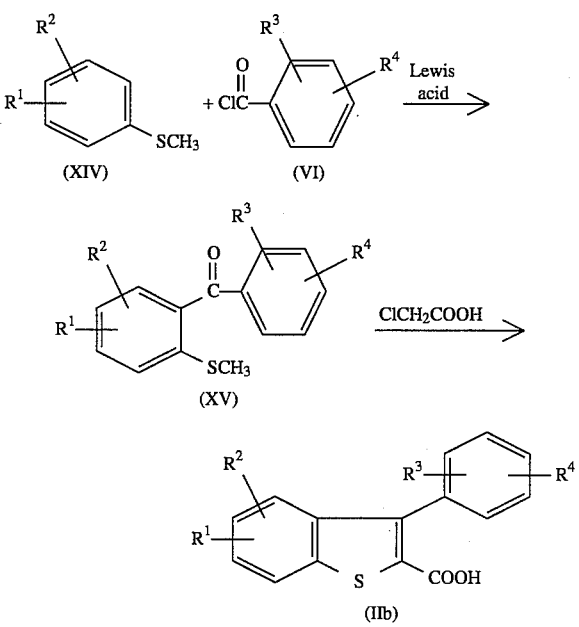

wherein $R^1$, $R^2$, $R^3$ and $R^4$ are as defined above.

In further detail, a compound (XIV) is reacted with a benzoyl chloride in the presence of a Lewis acid (e.g. aluminum chloride or tin tetrachloride) to obtain a compound (XV). Usually, this reaction can be carried out by the use of or without a solvent (e.g. carbon disulfide or nitrobenzene) in a temperature range of room temperature to about 100° C. Then, the compound (XV) is reacted with chloroacetic acid in a temperature range of approximately 80°–130° C. to obtain benzothiophene or a derivative thereof (IIb).

Process C (in the case where X=

The compound of the general formula (II) can be synthesized from a compound of the formula (XVI) by the process described in J. Org. Chem. 37, 3624 (1972) or a process based thereon.

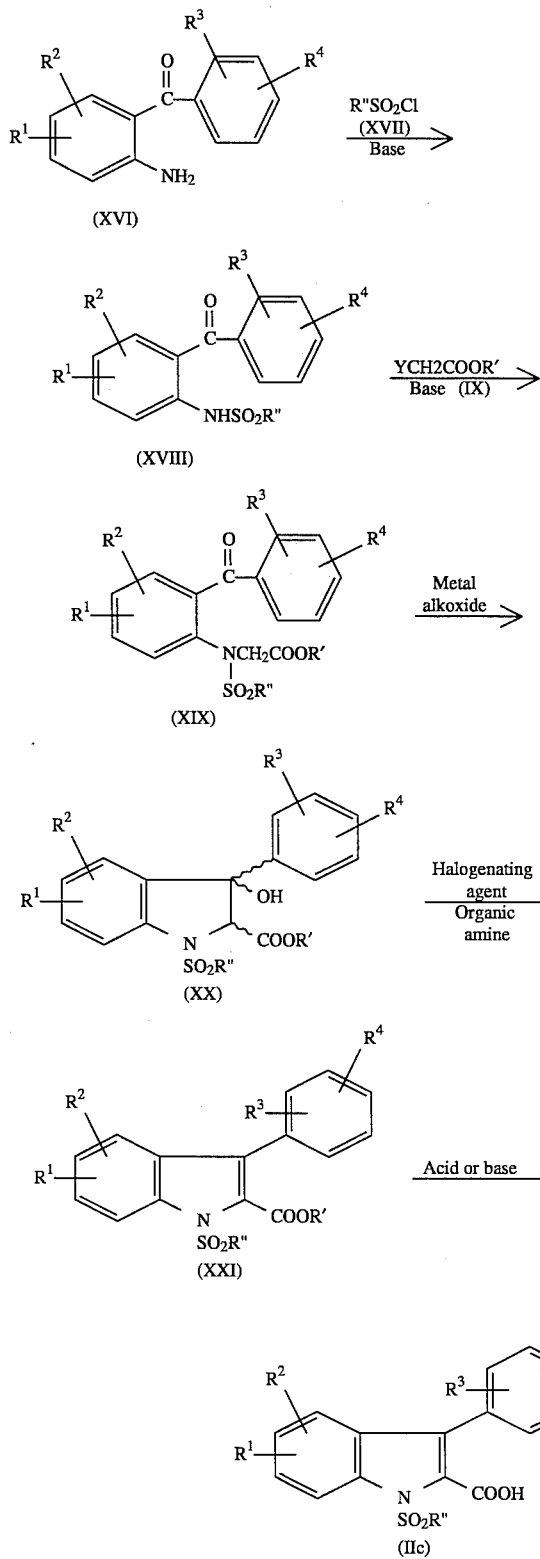

wherein $R^1$, $R^2$, $R^3$, $R^4$, R' and Y are as defined above, and R" is a phenyl group or a toluyl group.

In further detail, a 2-aminobenzophenone (XVI) is converted into a compound (XVIII) by a conventional method, and this compound is reacted with a compound (IX) in the presence of a metal hydride (e.g. sodium hydride or potassium hydride) in a solvent (e.g. dimethylformamide or dimethyl sulfoxide) in a temperature range of approximately 0°–50° C. to obtain a compound (XIX). Then, the compound (XIX) is reacted with a metal alkoxide (e.g. sodium methoxide, sodium ethoxide, sodium isopropoxide or potassium t-butoxide) in an ordinary solvent (e.g. methanol, ethanol, isopropanol or t-butanol) in a temperature range of room temperature to about 80° C. to obtain a compound (XX). Next, the compound (XX) is reacted with a halogenating agent (e.g. thionyl chloride or phosphorus oxychloride) in the presence of an organic amine such as pyridine or triethylamine in an inert solvent (e.g. benzene, toluene or xylene) in a temperature range of approximately 0°–50° C. to obtain a compound (XXI). Subsequently, the compound (XXI) is hydrolyzed with an acid or an alkali to obtain a compound (IIc).

Process D (in the case where X=—NR—)

The compound of the general formula (II) can be synthesized by the process described in J. Org. Chem. 37, 3624 (1972) or a process based thereon, by using a compound of the formula (XXII) synthesized according to Japanese Patent Unexamined Publication No. 3-130252, as a starting material.

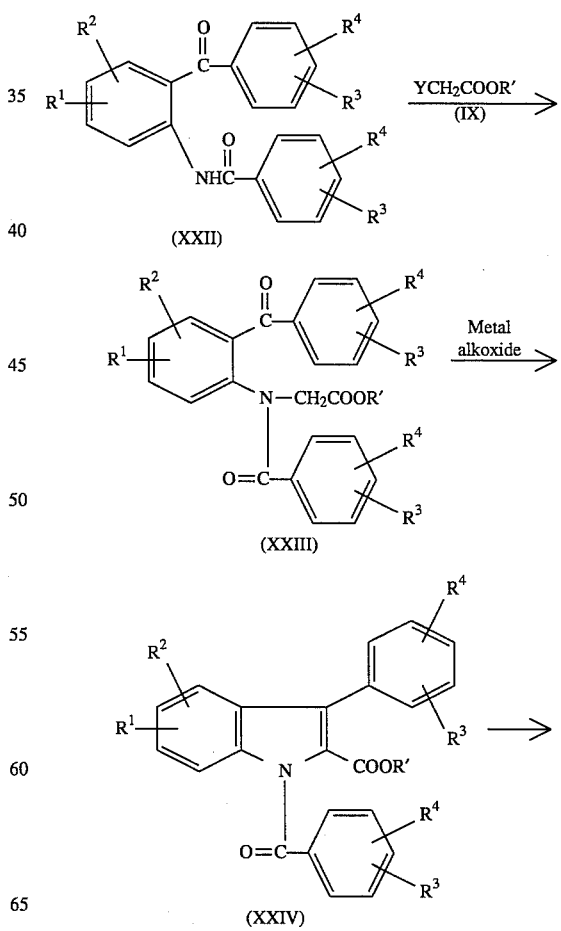

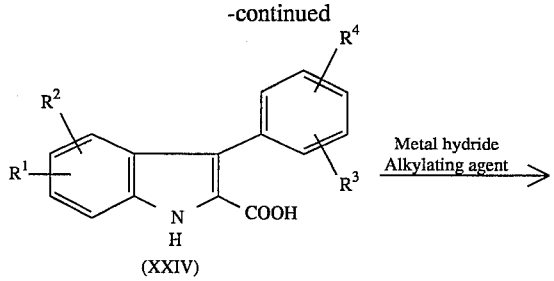

(XXIV)

Metal hydride
Alkylating agent →

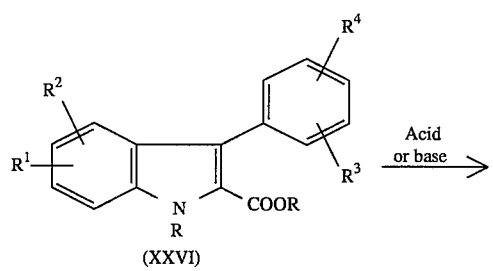

(XXVI)

Acid or base →

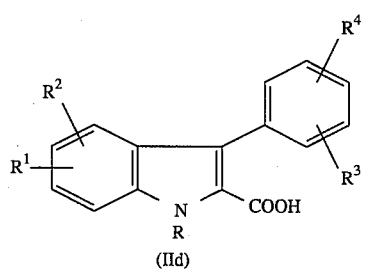

(IId)

wherein $R^1$, $R^2$, $R^3$, $R^4$, R' and Y are as defined above, and R is a lower alkyl group.

In further detail, a compound (XXIV) is obtained from the compound (XXII) through a compound (XXIII) by the same process as the production process of the compound (XXI). The obtained compound (XXIV) is hydrolyzed with an aqueous alkali metal hydroxide solution such as sodium hydroxide or potassium hydroxide in a solvent such as methanol, ethanol, isopropanol or t-butanol in a temperature range of room temperature to about 80° C. to obtain a carboxylic acid (XXV). Then, the carboxylic acid (XXV) is reacted with an alkylating agent (e.g. an alkyl iodide, alkyl bromide or dialkyl sulfate) in the presence of a metal hydride (e.g. sodium hydride or potassium hydride) in a solvent (e.g. dimethylformamide or dimethyl sulfoxide) in a temperature range of approximately 0°–50° C. to obtain a compound (XXVI). Subsequently, the compound (XXVI) is hydrolyzed under alkaline conditions to obtain a compound (IId).

Specific examples of compounds of the general formula (I) obtained by the above production processes are given in Table 1.

In the Table, the following abbreviations are used to stand for the substituent groups as specified below:
Me; methyl,
Et; ethyl,
iPr; isopropyl,
t-Bu; tert-butyl,
nHex; n-hexane, and
Tos; toluenesulfonyl.

TABLE 1

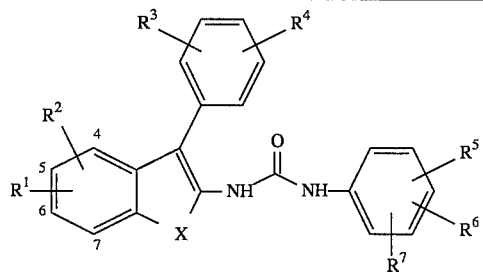

| Compound No. | X | $R^1$ | $R^2$ | $R^3$ | $R^4$ | $R^5$ | $R^6$ | $R^7$ |
|---|---|---|---|---|---|---|---|---|
| 1 | O | 5-F | H | 2-Cl | H | 2-Et | 6-Et | H |
| 2 | O | 5-F | H | 2-Cl | H | 2-iPr | 6-iPr | H |
| 3 | O | 5-F | H | 2-Cl | H | 2-F | 4-F | H |
| 4 | O | 5-Cl | H | 2-Cl | H | H | H | H |
| 5 | O | 5-Cl | H | 2-Cl | H | 2-Me | H | H |
| 6 | O | 5-Cl | H | 2-Cl | H | 2-C(=CH$_2$)CH$_3$ | H | H |
| 7 | O | 5-Cl | H | 2-Cl | H | 2-CF$_3$ | H | H |
| 8 | O | 5-Cl | H | 2-Cl | H | 2-OMe | H | H |
| 9 | O | 5-Cl | H | 2-Cl | H | 2-SMe | H | H |
| 10 | O | 5-Cl | H | 2-Cl | H | 2-OMe | 4-OMe | 6-OMe |
| 11 | O | 5-Cl | H | 2-Cl | H | 2-Me | 6-Me | H |
| 12 | O | 5-Cl | H | 2-Cl | H | 2-Et | 6-Et | H |
| 13 | O | 5-Cl | H | 2-Cl | H | 2-iPr | 6-iPr | H |
| 14 | O | 5-Cl | H | 2-Cl | H | 2-Et | 6-Me | H |
| 15 | O | 5-Cl | H | 2-Cl | H | 2-iPr | 6-Me | H |

TABLE 1-continued

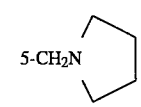

| Compound No. | X | R¹ | R² | R³ | R⁴ | R⁵ | R⁶ | R⁷ |
|---|---|---|---|---|---|---|---|---|
| 16 | O | 5-Cl | H | 2-Cl | H | 2-t-Bu | 6-Me | H |
| 17 | O | 5-Cl | H | 2-Cl | H | 2-F | 4-F | H |
| 18 | O | 5-Cl | H | 2-Cl | H | 2-Br | 6-Br | H |
| 19 | O | 5-Cl | H | 2-Cl | H | 2-NMe₂ | 6-Me | H |
| 20 | O | 5-Me | H | H | H | 2-iPr | 6-iPr | H |
| 21 | O | 5-Me | H | 2-Cl | H | 2-Et | 6-Et | H |
| 22 | O | 5-Me | H | 2-Cl | H | 2-iPr | 6-iPr | H |
| 23 | O | 5-Me | H | 2-Cl | H | 2-F | 4-F | H |
| 24 | O | 5-Et | H | 2-Cl | H | 2-Et | 6-Et | H |
| 25 | O | 5-Et | H | 2-Cl | H | 2-iPr | 6-iPr | H |
| 26 | O | 5-Et | H | 2-Cl | H | 2-F | 4-F | H |
| 27 | O | 5-nHex | H | 2-Cl | H | 2-iPr | 6-iPr | H |
| 28 | O | 5-nHex | H | 2-Cl | H | 2-F | 4-F | H |
| 29 | O | 5-OMe | H | 2-Cl | H | 2-Et | 6-Et | H |
| 30 | O | 5-OMe | H | 2-Cl | H | 2-iPr | 6-iPr | H |
| 31 | O | 5-OMe | H | 2-Cl | H | 2-F | 4-F | H |
| 32 | O | 5-CH₂NMe₂ | H | 2-Cl | H | 2-iPr | 6-iPr | H |
| 33 | O | 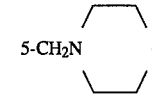 | H | 2-Cl | H | 2-iPr | 6-iPr | H |
| 34 | O | 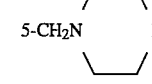 | H | 2-Cl | H | 2-iPr | 6-iPr | H |
| 35 | O | 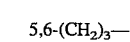 | H | 2-Cl | H | 2-iPr | 6-iPr | H |
| 36 | O | 5-Me | 6-Me | 2-Cl | H | 2-Me | 6-Me | H |
| 37 | O | 5-Me | 6-Me | 2-Cl | H | 2-Et | 6-Et | H |
| 38 | O | 5-Me | 6-Me | 2-Cl | H | 2-iPr | 6-iPr | H |
| 39 | O | 5-Me | 6-Me | 2-Cl | H | 2-iPr | 6-Me | H |
| 40 | O | 5-Me | 6-Me | 2-Cl | H | 2-F | 4-F | H |
| 41 | O | 5-Me | 7-Me | 2-Cl | H | 2-Me | 6-Me | H |
| 42 | O | 5-Me | 7-Me | 2-Cl | H | 2-Et | 6-Et | H |
| 43 | O | 5-Me | 7-Me | 2-Cl | H | 2-iPr | 6-iPr | H |
| 44 | O | 5-Me | 7-Me | 2-Cl | H | 2-iPr | 6-Me | H |
| 45 | O | 5-Me | 7-Me | 2-Cl | H | 2-Me | 4-Me | 6-Me |
| 46 | O | 5-Me | 7-Me | 2-Cl | H | 2-F | 4-F | H |
| 47 | O | 5-Me | 7-Me | 2-Cl | H | 2-F | 6-F | H |
| 48 | O | 5-Me | 7-Me | 2-Cl | H | 2-F | 4-F | 6-F |
| 49 | O | 5-Me | 7-Me | 2-Cl | H | 2-Cl | 6-Cl | H |
| 50 | O | 5-Me | 7-Me | 2-Cl | H | 4-NMe₂ | H | H |
| 51 | O | 5,6-(CH₂)₃— | | 2-Cl | H | 2-Me | 6-Me | H |
| 52 | O | 5,6-(CH₂)₃— | | 2-Cl | H | 2-Et | 6-Et | H |
| 53 | O | 5,6-(CH₂)₃— | | 2-Cl | H | 2-iPr | 6-iPr | H |
| 54 | O | 5,6-(CH₂)₃— | | 2-Cl | H | 2-Me | 4-Me | 6-Me |
| 55 | O | 5,6-(CH₂)₃— | | 2-Cl | H | 2-F | 4-F | H |
| 56 | O | 5,6-(CH₂)₃— | | 2-Cl | H | 2-F | 4-F | 6-F |
| 57 | O | 5-Cl | H | 2-F | H | 2-Et | 6-Et | H |
| 58 | O | 5-Cl | H | 2-F | H | 2-iPr | 6-iPr | H |
| 59 | O | 5-Cl | H | 2-F | H | 2-F | 4-F | H |
| 60 | O | 5-Cl | H | 2-Me | H | 2-Et | 6-Et | H |
| 61 | O | 5-Cl | H | 2-Me | H | 2-iPr | 6-iPr | H |
| 62 | O | 5-Cl | H | 2-SMe | H | 2-Et | 6-Et | H |
| 63 | O | 5-Cl | H | 2-SMe | H | 2-iPr | 6-iPr | H |
| 64 | S | 5-Cl | H | 2-Cl | H | 2-Me | 6-Me | H |

TABLE 1-continued

| Compound No. | X | R¹ | R² | R³ | R⁴ | R⁵ | R⁶ | R⁷ |
|---|---|---|---|---|---|---|---|---|
| 65 | S | 5-Cl | H | 2-Cl | H | 2-Et | 6-Et | H |
| 66 | S | 5-Cl | H | 2-Cl | H | 2-iPr | 6-iPr | H |
| 67 | S | 5-Cl | H | 2-Cl | H | 2-iPr | 6-Me | H |
| 68 | S | 5-Cl | H | 2-Cl | H | 2-F | 4-F | H |
| 69 | S | 5-Cl | H | 2-Cl | H | 2-F | 6-F | H |
| 70 | S | 5-Cl | H | 2-Cl | H | 2-F | 6-F | 6-F |
| 71 | S | 5-Cl | H | 2-Cl | H | 2-Cl | 6-Cl | H |
| 72 | S | 5-Me | H | 2-Cl | H | 2-Et | 6-Et | H |
| 73 | S | 5-Me | H | 2-Cl | H | 2-iPr | 6-iPr | H |
| 74 | S | 5-Me | H | 2-Cl | H | 2-iPr | 6-Me | H |
| 75 | S | 5-Me | H | 2-Cl | H | 2-F | 4-F | H |
| 76 | S | 5-iPr | H | 2-Cl | H | 2-Et | 6-Et | H |
| 77 | S | 5-iPr | H | 2-Cl | H | 2-iPr | 6-iPr | H |
| 78 | S | 5-iPr | H | 2-Cl | H | 2-F | 4-F | H |
| 79 | S | 5-Me | 6-Me | 2-Cl | H | 2-Me | 4-Me | H |
| 80 | S | 5-Me | 6-Me | 2-Cl | H | 2-Et | 6-Et | H |
| 81 | S | 5-Me | 6-Me | 2-Cl | H | 2-iPr | 6-iPr | H |
| 82 | S | 5-Me | 6-Me | 2-Cl | H | 2-iPr | 6-Me | H |
| 83 | S | 5-Me | 6-Me | 2-Cl | H | 2-NMe₂ | 6-Me | H |
| 84 | S | 5-Me | 6-Me | 2-Cl | H | 2-F | 4-F | H |
| 85 | S | 5-Me | 6-Me | 2-Cl | H | 2-F | 4-Me | H |
| 86 | S | 5-Me | 6-Me | 2-Cl | H | 2-OMe | 4-OMe | 6-OMe |
| 87 | S | 5,6-(CH₂)₃— | | 2-Cl | H | 2-Me | 6-Me | H |
| 88 | S | 5,6-(CH₂)₃— | | 2-Cl | H | 2-Et | 6-Et | H |
| 89 | S | 5,6-(CH₂)₃— | | 2-Cl | H | 2-iPr | 6-iPr | H |
| 90 | S | 5,6-(CH₂)₃— | | 2-Cl | H | 2-iPr | 6-Me | H |
| 91 | S | 5,6-(CH₂)₃— | | 2-Cl | H | 2-NMe₂ | 6-Me | H |
| 92 | S | 5,6-(CH₂)₃— | | 2-Cl | H | 2-F | 4-F | H |
| 93 | S | 5,6-(CH₂)₃— | | 2-Cl | H | 2-F | 6-F | H |
| 94 | S | 5,6-(CH₂)₃— | | 2-Cl | H | 2-F | 4-F | 6-F |
| 95 | S | 5,6-(CH₂)₃— | | 2-Cl | H | 2-Cl | 6-Cl | H |
| 96 | S | 5,6-(CH₂)₄— | | 2-Cl | H | 2-Et | 6-Et | H |
| 97 | S | 5,6-(CH₂)₄— | | 2-Cl | H | 2-iPr | 6-iPr | H |
| 98 | S | 5,6-(CH₂)₄— | | 2-Cl | H | 2-iPr | 6-Me | H |
| 99 | S | 5,6-(CH₂)₄— | | 2-Cl | H | 2-F | 4-F | H |
| 100 | S | 5-NO₂ | H | 2-Cl | 4-Cl | 2-iPr | 6-iPr | H |
| 101 | S | 5-NO₂ | H | 2-Cl | 4-Cl | 2-F | 4-F | H |
| 102 | S | 5-OMe | 6-OMe | 2-Cl | H | 2-Et | 6-Et | H |
| 103 | S | 5-OMe | 6-OMe | 2-Cl | H | 2-iPr | 6-iPr | H |
| 104 | S | 5-OMe | 6-OMe | 2-Cl | H | 2-iPr | 6-Me | H |
| 105 | S | 5-OMe | 6-OMe | 2-Cl | H | 2-F | 4-F | H |
| 106 | S | 5,6-(CH₂)₃— | | 2-Cl | 4-Cl | 2-iPr | 6-iPr | H |
| 107 | S | 5,6-(CH₂)₃— | | 2-Cl | 4-Cl | 2-F | 4-F | H |
| 108 | S | 5,6-(CH₂)₃— | | 2-F | H | 2-Et | 6-Et | H |
| 109 | S | 5,6-(CH₂)₃— | | 2-Me | H | 2-Et | 6-Et | H |
| 110 | S | 5,6-(CH₂)₃— | | 2-Me | H | 2-iPr | 6-iPr | H |
| 111 | S | 5,6-(CH₂)₃— | | 2-Me | H | 2-iPr | 6-Me | H |
| 112 | S | 5,6-(CH₂)₃— | | 2-Me | H | 2-F | 4-F | H |
| 113 | S | 5,6-(CH₂)₃— | | 2-CF₃ | H | 2-Et | 6-Et | H |
| 114 | S | 5,6-(CH₂)₃— | | 2-CF₃ | H | 2-iPr | 6-iPr | H |
| 115 | S | 5,6-(CH₂)₃— | | 2-CF₃ | H | 2-F | 4-F | H |
| 116 | S | 5,6-(CH₂)₃— | | 2-OMe | H | 2-Et | 6-Et | H |
| 117 | S | 5,6-(CH₂)₄— | | 2-Me | H | 2-Et | 6-Et | H |
| 118 | S | 5,6-(CH₂)₄— | | 2-Me | H | 2-iPr | 6-iPr | H |
| 119 | S | 5,6-(CH₂)₄— | | 2-Me | H | 2-F | 4-F | H |
| 120 | N-ToS | H | H | H | H | 2-F | 4-F | H |
| 121 | N-ToS | 5-Me | 7-Me | 2-Cl | H | 2-iPr | 6-Me | H |
| 122 | N-ToS | 5-Me | 7-Me | 2-Cl | H | 2-F | 4-F | H |
| 123 | NMe | 5-Me | 7-Me | 2-Cl | H | 2-iPr | 6-Me | H |
| 124 | NMe | 5-Me | 7-Me | 2-Cl | H | 2-F | 4-F | H |
| 125 | NMe | 5-Me | 7-Me | 2-Cl | H | 4-NMe₂ | H | H |

Examples, reference examples, formulation examples and test examples of the present invention are described below but should not be construed as limiting the scope of the invention.

Example 1

N-[3-(2-(Chlorophenyl)-5-fluorobenzofuran-2-yl]-N'-(2,6-diethylphenyl)urea (compound 1)

To a stirred mixture of 436 mg of 3-(2 -chlorophenyl)-5-fluorobenzofuran-2-carboxylic acid and 0.36 cc of diphenylphosphoryl azide in 4 cc of benzene was added dropwise 0.23 cc of triethylamine at room temperature. The resulting mixture was stirred at room temperature for 30 minutes and then heated under reflux for 10 minutes. After cooling, 0.28 cc of 2,6-diethylaniline was added, followed by refluxing for 3 hours. After cooling, water was added to the reaction mixture and extracted with chloroform. The extract was dried over magnesium sulfate, and distilled to remove the solvent. The crude product thus obtained was purified by a silica gel column chromatography (eluent: chloroform) to obtain 400 mg of compound 1.

Yield 61.0%, m.p. 218°–219° C.

NMR ($\delta$, ppm; DMSO-$d_6$)

1.08 (t, 6H), 2.47 (q, 4H), 7.05–7.15 (m, 5H), 7.44–7.64 (m, 5H), 7.89 (s, 1H), 9.15 (s, 1H).

The compounds described in Examples 2 to 20 were obtained in the same manner as in Example 1.

Example 2

N-[3-( 2-Chlorophenyl )-5-fluorobenzofuran-2-yl]-N'-(2,6-diisopropylphenyl)urea (compound 2)

Yield 40.8%, m.p. 230°–231° C.

NMR ($\delta$, ppm; DMSO-$d_6$) 1.10 (d, 12H), 3.06 (m, 2H), 7.10–7.22 (m, 5H), 7.44–7.63 (m, 5H), 7.88 (s, 1H), 9.12 1H).

Example 3

N-[3-(2-Chlorophenyl)-5-fluorobenzofuran-2-yl]-N'-(2, 4-difluorophenyl)urea (compound 3)

Yield 52.9%, m.p. 196°–198° C.

NMR ($\delta$, ppm; DMSO-$d_6$) 7.03–7.16 (m, 5H), 7.46–7.65 (m, 5H), 8.74 (s, 1H), 9.31 (d, 1H).

Example 4

N-[5-Chloro-3-(2-chlorophenyl)benzofuran-2-yl]-N'-phenylurea (compound 4)

Yield 54.6%, m.p. 193°–195° C.

NMR ($\delta$, ppm; DMSO-$d_6$) 6.99 (t, 1H), 7.23–7.67 (m, 11H), 8.90 (s, 1H), 9.07 (s, 1H).

Example 5

N-[5-Chloro-3-(2-chlorophenyl)benzofuran-2-yl]-N'-(2-methylphenyl)urea (compound 5)

Yield 57.6%, m.p. 234°–235° C.

NMR ($\delta$, ppm; DMSO-$d_6$) 2.17 (s, 3H), 6.98 (t, 1H), 7.15 (q, 2H), 7.27 (d, 1H), 7.33 (dd, 1H), 7.47–7.66 (m, 4H) , 8.16 (s, 1H), 9.36 (s, 1H).

Example 6

N-[5-Chloro-3-(2-chlorophenyl)benzofuran-2-yl]-N'-(2-isopropenylphenyl)urea (compound 6)

Yield 25.8%, m.p. 191°–194° C.

NMR ($\delta$, ppm; DMSO-$d_6$) 1.99 (s, 3H), 4.95 (s, 1H), 5.28 (d, 1H), 7.04–7.36 (m, 5H) , 7.46–7.72 (m, 6H), 7.98 1H), 9.55 (s, 1H).

Example 7

N-[5-Chloro-3-(2-chlorophenyl)benzofuran-2-yl]-N'-(2-trifluoromethylphenyl)urea (compound 7)

Yield 30.1%, m.p. 225°–226° C.

NMR ($\delta$, ppm; DMSO-$d_6$)

7.28 (d, 1H), 7.33 (dt, 2H), 7.45–7.60 (m, 3H), 7.60–7.72 (m, 4H), 7.78 (t, 1H), 8.32 (d, 1H), 9.80 (d, 1H).

Example 8

N-[5-Chloro-3-(2-chlorophenyl)benzofuran-2-yl]-N'-(2-methoxyphenyl)urea (compound 8)

Yield 50.8%, m.p. 231°–232° C.

NMR ($\delta$, ppm; DMSO-$d_6$) 3.85 (s, 3H), 6.88 (t, 1H), 7.00 (q, 2H), 7.25 (d, 1H), 7.34 (dd, 1H), 7.47–7.57 (m, 3H), 7.63–7.66 (m, 2H), 8.01 (d, 1H), 8.45 (s, 1H), 9.64 (s, 1H).

Example 9

N-[5-Chloro-3-(2-chlorophenyl)benzofuran-2-yl]-N'-(2-methylthiophenyl)urea (compound 9)

Yield 14.1%, m.p. 189°–191° C.

NMR ($\delta$, ppm; DMSO-$d_6$) 2.40 (s, 3H), 7.08–7.24 (m, 2H), 7.28–7.40 (m, 2H), 7.47–7.54 (m, 4H), 7.63–7.74 (m, 3H) , 8.35 (s, 1H), 9.76 (s, 1H).

Example 10

N- [5-Chloro-3-(2-chlorophenyl)benzofuran-2-yl]-N'-2,4,6-trimethoxyphenyl)urea (compound 10)

Yield 41.0%, m.p. 228°–229° C.

NMR ($\delta$, ppm; DMSO-$d_6$) 3.07 (s, 6H), 3.77 (s, 3H), 6.22 (s, 2H), 7.23 (d, 1H), 7.30–7.36 (m, 2H), 7.46–7.49 (m, 2H), 7.53–7.54 (m, 1H), 7.60–7.62 (m, 2H) , 8.80 (br, 1H).

Example 11

N- [5-Chloro-3-(2-chlorophenyl)benzofuran-2-yl]-N'-(2,6-dimethylphenyl)urea (compound 11)

Yield 48.2%, m.p. 249°–251° C.

NMR ($\delta$, ppm; DMSO-$d_6$) 2.11 (s, 6H), 7.04 (s, 3H), 7.27 (d, 1H), 7.34 (dd, 1H) , 7.46 (t, 1H), 7.56 (t, 1H), 7.60–7.66 (m, 2H), 7.98 (s, 1H), 9.25 (s, 1H).

Example 12

N-[5-Chloro-3-(2-chlorophenyl)benzofuran-2-yl]-N'-(2,6-diethylphenyl)urea (compound 12 )

Yield 47.6%, m.p. 222° C.

NMR ($\delta$, ppm; DMSO-$d_6$) 1.08 (t, 6H), 2.47 (q, 4H), 7.06 (d, 2H), 7.15 (t, 1H), 7.27 (d, 1H), 7.34 (dd, 1H), 7.45–7.63 (m, 3H), 7.61–7.66 (m, 2H), 7.92 (s, 1H), 9.21 (s, 1H).

Example 13

N-[5-Chloro-3-(2-chlorophenyl)benzofuran-2-yl]-N'-(2,6-diisopropylphenyl)urea (compound 13)

Yield 50.5%, m.p. 242°–243° C.

NMR ($\delta$, ppm; DMSO-$d_6$) 1.10 (d, 12H), 3.06 (m, 2H), 7.11 (d, 2H), 7.20–7.35 (m, 3H), 7.48–7.53 (m, 3H), 7.62–7.66 (m, 2H), 7.91 (s, 1H), 9.18 (s, 1H).

Example 14

N-[5-Chloro-3-(2-chlorophenyl)benzofuran-2-yl]-N'-(2-ethyl-6-methylphenyl)urea (compound 14)

Yield 26.4%, m.p. 228°–230° C.

NMR (δ, ppm; DMSO-$d_6$) 1.07 (t, 3H), 2.10 (s, 3H), 2.49 (q, 2H), 7.04–7.08 (m, 3H), 7.27–7.35 (m, 2H), 7.45–7.53 (m, 3H), 7.63–7.65 (m, 2H), 7.94 (s, 1H), 9.23 (s, 1H).

Example 15

N-[5-Chloro-3-(2-chlorophenyl)benzofuran-2-yl]-N'-(2-isopropyl-6-methylphenyl)urea (compound 15)

Yield 53.6%, m.p. 222°–223° C.

NMR (δ, ppm; DMSO-$d_6$) 1.09 (d, 6H), 2.10 (s, 3H), 3.08 (m, 1H), 7.00–7.20 (m, 3H), 7.20–7.40 (m, 2H), 7.40–7.70 (m, 5H), 7.92 (s, 1H), 9.27 (s, 1H).

Example 16

N-(2-t-Butyl-6-methylphenyl)-N'-[5-chloro-3-(2-chlorophenyl)benzofuran-2-yl]urea (compound 16)

Yield 21.8%, m.p.. 218°–220° C.

NMR (δ, ppm; DMSO-$d_6$) 1.29 (s, 9H), 2.05 (s, 3H), 7.09–7.25 (m, 5H), 7.32–7.65 (m, 5H), 7.77 (d, 1H), 9.25 (d, 1H).

Example 17

N-[5-Chloro-3-(2-chlorophenyl)benzofuran-2-yl]-N'-(2,4-difluorophenyl)urea (compound 17)

Yield 44.1%, m.p. 222°–223° C.

NMR (δ, ppm; DMSO-$d_6$) 7.04 (t, 1H), 7.27–7.37 (m, 3H), 7.47–7.56 3H), 7.64–7.67 (m, 2H), 7.92 (m, 1H), 8.75 (s, 1H), 9.36 (d, 1H).

Example 18

N-[5-Chloro-3-(2-chlorophenyl)benzofuran-2-yl]-N'-(2,6-dibromophenyl)urea (compound 18)

Yield 19.6%, m.p. 217°–219° C.

NMR (δ, ppm; DMSO-$d_6$) 7.16–7.37 (m, 3H), 7.45–7.76 (m, 7H), 9.54 1H), 9.35 (s, 1H).

Example 19

N-[5-chloro-3-(2-chlorophenyl)benzofuran-2-yl]-N'-(2-dimethylamino-6-methylphenyl)urea (compound Yield 38.6%, m.p. 185°–186° C.

NMR (δ, ppm; DMSO-$d_6$) 2.05 (s, 3H), 2.53 (s, 6H), 6.83–6.89 (m, 2H), 7.05 (m, 1H), 7.25 (d, 1H), 7.34 (m, 1H), 7.40–7.50 (m, 3H), 7.60–7.66 (m, 2H), 7.80 (s, 1H), 9.36 (s, 1H).

Example 20

N-(2,6-Diisopropylphenyl)-N,-(5-methyl-3-phenylbenzofuran-2-yl)urea (compound 20)

Yield 15.5%, m.p. 223°–225° C.

NMR (δ, ppm; DMSO-$d_6$) 1.13 (d, 12H), 2.41 (s, 3H), 3.14 (m, 2H), 7.12–7.23 (m, 4H), 7.48–7.52 (m, 5H), 7.68 (d, 2H), 7.96 (s, 1H), 8.34 (s, 1H).

Example 21

N-[3-(2-Chlorophenyl)-5-methylbenzofuran-2-yl]-N'-(2,6-diethylphenyl)urea (compound 21)

To a stirred mixture of 430 mg of 3-(2-chlorophenyl)-5-methylbenzofuran-2-carboxylic acid and 0.39 cc of diphenylphosphoryl azide in 6 cc of benzene was added dropwise 0.22 cc of triethylamine at room temperature. The resulting mixture was stirred at room temperature for 35 minutes and then heated under reflux for 15 minutes. After cooling, 0.30 cc of 2,6-diethylaniline was added, followed by refluxing for 2 hours. After cooling, water was added to the reaction mixture and extracted with chloroform. The extract was dried over magnesium sulfate, and distilled to remove the solvent. The crude product thus obtained was purified by a silica gel column chromatography (eluent: chloroform) to obtain 446 mg of compound 21.

Yield 68.7%, m.p. 214°–215° C.

NMR (δ, ppm; DMSO-$d_6$) 1.08 (t, 6H), 2.36 (s, 3H), 2.47 (q, 4H), 7.05–7.18 (m, 5H), 7.44–7.50 (m, 3H), 7.53 (m, 1H), 7.61 (m, 1H), 7.85 (s, 1H), 8.98 (s, 1H).

The compounds described in Examples 22 to 35 were obtained in the same manner as in Example 21.

Example 22

N-[3-(2-Chlorophenyl)-5-methylbenzofuran-2-yl]-N'-(2,6-diisopropylphenyl)urea (compound 22)

Yield 52.1%, m.p. 232°–234° C.

NMR (δ, ppm; DMSO-$d_6$) 1.10 (d, 12H), 3.06 (m, 2H), 7.09–7.13 (m, 4H), 7.22 (t, 1H), 7.44–7.48 (m, 3H), 7.52 (m, 1H), 7.62 (m, 1H), 7.84 (s, 1H), 8.95 (s, 1H).

Example 23

N-[3-(2-Chlorophenyl)-5-methylbenzofuran-2-yl]-N'-(2,4-difluorophenyl)urea (compound 23)

Yield 72.7%, m.p. 179°–180° C.

NMR (δ, ppm; DMSO-$d_6$) 2.37 (s, 3H), 7.01–7.15 (m, 3H), 7.31 (t, 1H), 7.45–7.53 (m, 4H), 7.64 (m, 1H), 7.93 (m, 1H), 8.72 (s, 1H), 9.15 (s, 1H).

Example 24

N-[3-(2-Chlorophenyl)-5-ethylbenzofuran-2-yl]-N'-(2,6-diethylphenyl)urea (compound 24)

Yield 52.4%, m.p. 195°–197° C.

NMR (δ, ppm; DMSO-$d_6$) 1.06 (t, 6H), 1.17 (t, 3H), 2.47 (q, 4H), 2.66 (q, 2H), 6.99–7.16 (m, 5H), 7.42–7.54 (m, 4H), 7.61 (m, 1H), 7.84 (s, 1H), 8.97 (s, 1H).

Example 25

N-[3-(2-Chlorophenyl)-5-ethylbenzofuran-2-yl]-N'-(2,6-diisopropylphenyl)urea (compound 25)

Yield 47.6%, m.p. 233°–234° C.

NMR (δ, ppm; DMSO-$d_6$) 1.09 (d, 12H), 1.17 (t, 3H), 2.66 (q, 2H), 3.06 (m, 2H), 7.10–7.22 (m, 5H), 7.44–7.54 (m, 4H), 7.54–7.61 (m, 1H), 7.83 (s, 1H), 8.94 (s, 1H).

Example 26

N-[-3-(2-Chlorophenyl)-5-ethylbenzofuran-2-yl]-N'-(2,4-difluorophenyl)urea (compound 26)

Yield 39.6%, m.p. 167°–168 C.

NMR (δ, ppm; DMSO-$d_6$) 1.16 (t, 3H), 2.66 (q, 2H), 6.98–7.18 (m, 3H), 7.30–7.32 (m, 1H), 7.46–7.54 (m, 4H), 7.63–7.64 (m, 1H), 7.86–7.94 (m, 1H), 8.70 (s, 1H), 9.15 (d, 1H).

Example 27

N-[3-(2-Chlorophenyl)-5-n-hexylbenzofuran-2-yl]-N'-(2,6-diisopropylphenyl)urea (compound 27)

Yield 38.3%, m.p. 191°–192° C.

NMR (δ, ppm; DMSO-$d_6$) 0.84 (t, 3H), 1.11 (d, 12H), 1.21–1.36 (m, 6H), 1.55 (m, 2H), 2.63 (t, 2H), 3.07 (m, 2H), 7.08–7.15 (m, 4H), 7.22 (t, 1H), 7.44–7.49 (m, 3H), 7.54 (m, 1H), 7.62 (d, 1H), 7.85 (s, 1H), 8.95 (s, 1H).

Example 28

N-[3-(2-Chlorophenyl)-5-n-hexylbenzofuran-2-yl]-N'-(2,4-difluorophenyl)urea (compound 28)

Yield 68.2%, m.p. 149°–150° C.

NMR (δ, ppm; DMSO-$d_6$) 0.83 (t, 3H), 1.2–1.35 (m, 6H), 1.55 (m, 2H), 2.63 (t, 2H), 7.00–7.16 (m, 2H), 7.16 (d, 1H), 7.31 (m, 1H), 7.46–7.63 (m, 4H), 7.65 (m, 1H), 7.90 (m, 1H), 8.71 (s, 1H), 9.14 (d, 1H).

Example 29

N-[3-(2-Chlorophenyl)-5-methoxybenzofuran-2-yl]-N'-(2,6-diethylphenyl)urea (compound 29)

Yield 57.0%, m.p. 220°–222° C.

NMR (δ, ppm; DMSO-$d_6$) 1.08 (t, 6H), 2.47 (q, 4H), 3.73 (s, 3H), 6.74 (d, 1H), 6.90 (dd, 1H), 7.06 (d, 1H), 7.16 (t, 1H), 7.43–7.55 (m, 4H), 7.62 (d, 1H), 7.86 (s, 1H), 8.99 (s, 1H).

Example 30

N-[3-(2-Chlorophenyl)-5-methoxybenzofuran-2-yl]-N'-(2,6-diisopropylphenyl)urea (compound 30)

Yield 37.7%, m.p. 216°–217° C.

NMR (δ, ppm; DMSO-$d_6$) 1.11 (d, 12H), 3.06 (m, 2H), 3.73 (s, 3H), 6.75 (d, 1H), 6.90 (dd, 1H), 7.11 (d, 2H), 7.22 (t, 1H), 7.44–7.57 (m, 4H), 7.63 (d, 1H), 7.85 (s, 1H), 8.96 (s, 1H).

Example 31

N-[3-(2-Chlorophenyl)-5-methoxybenzofuran-2-yl]-N'-(2,4-difluorophenyl)urea (compound 31)

Yield 42.8%, m.p. 190°–191° C.

NMR (δ, ppm; DMSO-$d_6$) 3.74 (s, 3H), 6.74 (d, 1H), 6.92 (dd, 1H), 7.04 (dt, 1H), 7.31 (dt, 1H), 7.46–7.56 (m, 4H), 7.65 (m, 1H), 7.92 (m, 1H), 8.72 (s, 1H), 9.17 (d, 1H).

Example 32

N-[3-(2-Chlorophenyl)-5-dimethylaminomethylbenzofuran-2-yl]-N'-(2,6-diisopropylphenyl)urea (compound 32)

Yield 39.7%, m.p. 197°–199° C.

NMR (δ, ppm; DMSO-$d_6$) 1.10 (d, 12H), 2.12 (s, 6H), 3.07 (m, 2H), 3.44 (s, 2H), 7.11–7.25 (m, 5H), 7.45–7.65 (m, 5H), 7.86 (s, 1H), 8.98 (s, 1H).

Example 33

N-[3-(2-Chlorophenyl)-5-(1-pyrrolidino)methylbenzofuran-2-yl]-N'-(2,6-diisopropylphenyl)urea (compound 33)

Yield 31.3%, m.p. 178°–179° C.

NMR (δ, ppm; DMSO-$d_6$) 1.10 (d, 12H), 1.66 (m, 4H), 2.40 (m, 4H), 3.07 (m, 2H), 3.61 (s, 2H), 7.10–7.26 (m, 5H), 7.45–7.65 (m, 5H), 7.86 (s, 1H), 8.98 (s, 1s).

Example 34

N-[3-(2-Chlorophenyl)-5-(1-morpholino)methylbenzofuran-2-yl]-N'-(2,6-diisopropylphenyl)urea (compound 34)

Yield 26.1%, m.p. 133°–1350° C.

NMR (δ, ppm; DMSO-$d_6$) 1.11 (d, 12H), 2.33 (s, 4H), 3.07 (m, 2H), 3.52 (m, 6H), 7.10–7.27 (m, 5H), 7.45–7.62 (m, 5H), 7.85 (s, 1H), 8.98 (s, 1H).

Example 35

N-[3-(2-Chlorophenyl)-5-(4-methyl-1-piperazino)methylbenzofuran-2-yl]-N'-(2,6-diisopropylphenyl)urea (compound 35)

Yield 16.1%, m.p. 136°–137° C.

NMR (δ, ppm; DMSO-$d_6$) 1.10 (d, 12H), 2.22 (s, 3H), 2.40 (brs, 8H), 3.06 (m, 2H), 3.52 (m, 2H), 7.10–7.25 (m, 6H), 7.44–7.62 (m, 4H), 7.90 (s, 1H), 9.04 (s, 1H).

Example 36

N-[3-(2-Chlorophenyl)-5,6-dimethylbenzofuran-2-yl]-N'-(2,6-dimethylphenyl)urea (compound 36)

To a stirred mixture of 301 mg of 3-(2-chlorophenyl)-5,6-dimethylbenzofuran-2-carboxylic acid and 0.26 cc of diphenylphosphoryl azide in 5 cc of benzene was added dropwise 0.14 cc of triethylamine at room temperature. The resulting mixture was stirred at room temperature for 15 minutes and then heated under reflux for 15 minutes. After cooling, 0.14 cc of 2,6-dimethylaniline was added, followed by refluxing for 2 hours. After cooling, water was added to the reaction mixture and extracted with chloroform. The extract was dried over magnesium sulfate, and distilled to remove the solvent. The crude product thus obtained was purified by a silica gel column chromatography (eluent: chloroform) to obtain 279 mg of compound 36.

Yield 66.6%, m.p. 252°–254° C.

NMR (δ, ppm; DMSO-$d_6$) 2.11 (s, 6H), 2.26 (s, 3H), 2.33 (s, 3H), 7.05 (d, 4H), 7.37 (s, 1H), 7.43 (m, 2H), 7.54 (m, 1H), 7.62 (m, 1H), 7.89 (s, 1H), 8.90 (br, 1H).

The compounds described in Examples 37 to 59 were obtained in the same manner as in Example 36.

Example 37

N-[3-(2-Chlorophenyl)-5,6-dimethylbenzofuran-2-yl]-N'-(2,6-diethylphenyl)urea (compound 37)

Yield 62.6%, m.p. 228°–230° C.

NMR (δ, ppm; DMSO-$d_6$) 1.08 (t, 6H), 2.26 (s, 3H), 2.33 (s, 3H), 2.47 (q, 4H), 7.06 (d, 3H), 7.14 (t, 1H), 7.37 (s, 1H), 7.45 (m, 2H), 7.52 (m, 1H), 7.61 (m, 1H), 7.81 (s, 1H), 8.88 (s, 1H).

Example 38

N-[3-(2-Chlorophenyl)-5,6-dimethylbenzofuran-2-yl]-N'-(2,6-diisopropylphenyl)urea (compound 38)

Yield 41.1%, m.p. 249°–250° C.

NMR (δ, ppm; DMSO-$d_6$) 1.09 (d, 12H), 2.26 (s, 3H), 2.33 (s, 3H), 3.06 (m, 2H), 7.09 (m, 3H), 7.21 (t, 1H), 7.37 (s, 1H), 7.44 (m, 2H), 7.50 (m, 1H), 7.61 (dd, 1H), 7.81 (s, 1H), 8.85 (s, 1H).

Example 39

N-[2-[3-(2-Chlorophenyl)-5,6-dimethylbenzofuran-2-yl]-N'-(2,6-diisopropylphenyl)urea (compound 39)

Yield 53.5%, m.p. 218°–221° C.

NMR (δ, ppm; DMSO-$d_6$) 1.10 (d, 6H), 2.10 (s, 3H), 2.26 (s, 3H), 2.33 (s, 3H), 3.08 (m, 1H), 7.06 (m, 2H), 7.12 (m, 2H), 7.37 (s, 1H), 7.43 (m, 2H), 7.52 (m, 1H), 7.60 (m, 1H), 7.84 (s, 1H), 8.90 (s, 1H).

Example 40

N-[3-(2-Chlorophenyl)-5,6-dimethylbenzofuran-2-yl]-N'-(2,4-difluorophenyl)urea (compound 40)

Yield 54.8%, m.p. 205°–207° C.

NMR (δ, ppm; DMSO-d$_6$) 2.26 (s, 3H), 2.33 (s, 3H), 7.02 (m, 2H), 7.30 (dt, 1H), 7.38 (s, 1H), 7.47 (m, 4H), 7.61 (m, 1H), 7.91 (m, 1H), 8.69 (s, 1H), 9.06 (d, 1H).

Example 41

N-[3-(2-Chlorophenyl)-5,7-dimethylbenzofuran-2-yl]-N'-(2,6-dimethylphenyl)urea (compound 41)

Yield 65.4%, m.p. 243°–244° C.

NMR (δ, ppm; DMSO-d$_6$) 2.10 (s, 6H), 2.32 (s, 3H), 2.45 (s, 3H), 6.90 (s, 1H), 6.95 (s, 1H), 7.03 (s, 3H), 7.43 (m, 2H), 7.51 (m, 1H), 7.60 (m, 1H), 7.90 (s, 1H), 9.00 (br, 1H).

Example 42

N-[3-(2-Chlorophenyl)-5,7-dimethylbenzofuran-2-yl]-N'-(2,6-diethylphenyl)urea (compound 42)

Yield 63.7%, m.p. 223°–2240° C.

NMR (δ, ppm; DMSO-d$_6$) 1.07 (s, 6H), 2.32 (s, 3H), 2.45 (s, 3H), 2.47 (q, 4H), 6.90 (s, 1H), 6.95 (s, 1H), 7.05 (d, 2H), 7.15 (t, 1H), 7.43 (m, 2H), 7.50 (m, 1H), 7.62 (m, 1H), 7.86 (s, 1H), 8.98 (s, 1H).

Example 43

N-[3-(2-Chlorophenyl)-5,7-dimethylbenzofuran-2-yl]-N'-(2,6-diisopropylphenyl)urea (compound 43)

Yield 84.2%, m.p. 208°–210° C.

NMR (δ, ppm; DMSO-d$_6$) 1.09 (d, 12H), 2.32 (s, 3H), 2.45 (s, 3H), 3.06 (m, 2H), 6.90 (s, 1H), 6.95 (s, 1H), 7.10 (d, 2H), 7.21 (t, 1H), 7.43 (m, 2H), 7.50 (m, 1H), 7.60 (m, 1H), 7.85 (s, 1H), 8.96 (s, 1H).

Example 44

N-[3-(2-Chlorophenyl)-5,7-dimethylbenzofuran-2-yl]-N'-(2-isopropyl-6-methylphenyl)urea (compound 44)

Yield 69.4%, m.p. 227°–228° C.

NMR (δ, ppm; DMSO-d$_6$) 1.08 (d, 6H), 2.08 (s, 3H), 2.32 (s, 3H), 2.45 (s, 3H), 3.08 (m, 1H), 6.89 (s, 1H), 6.95 (s, 1H), 7.03 (m, 1H), 7.11 (m, 2H), 7.43 (m, 2H), 7.51 (m, 1H), 7.60 (m, 1H), 7.86 (s, 1H), 9.00 (s, 1H).

Example 45

N-[3-(2-Chlorophenyl)-5,7-dimethylbenzofuran-2-yl]-N'-(2,4,6-trimethylphenyl)urea (compound 45)

Yield 73.2%, m.p. 248°–249° C.

NMR (δ, ppm; DMSO-d$_6$) 2.06 (s, 6H), 2.20 (s, 3H), 2.32 (s, 3H), 2.44 (s, 3H), 6.84 (s, 2H), 6.90 (s, 1H), 6.95 (s, 1H), 7.42 (m, 2H), 7.52 (m, 1H), 7.60 (m, 1H), 7.80 (s, 1H), 8.97 (br, 1H).

Example 46

N-[3-(2-Chlorophenyl)-5,7-dimethylbenzofuran-2-yl]-N'-(2,4-difluorophenyl)urea (compound 46)

Yield 71.6%, m.p. 212°–214° C.

NMR (δ, ppm; CDCl$_3$) 2.38 (s, 3H), 2.55 (s, 3H), 6.80 (s, 1H), 6.83–6.92 (m, 2H), 6.97 (d, 2H), 7.36–7.42 (m, 2H), 7.44–7.48 (m, 1H), 7.52–7.58 (m, 1H), 8.07–8.17 (m, 2H).

Example 47

N-[3-(2-Chlorophenyl)-5,7-dimethylbenzofuran-2-yl]-N'-(2,6-difluorophenyl)urea (compound 47)

Yield 59.7%, m.p. 223°–224° C.

NMR (δ, ppm; DMSO-d$_6$) 2.32 (s, 3H), 2.44 (s, 3H), 6.90 (s, 1H), 6.97 (s, 1H), 7.13 (m, 2H), 7.31 (m, 1H), 7.45 (m, 2H), 7.52 (m, 1H), 7.63 (m, 1H), 8.35 (s, 1H), 9.14 (s, 1H).

Example 48

N-[3-(2-Chlorophenyl)-5,7-dimethylbenzofuran-2-yl]-N'-(2,4,6-trifluorophenyl)urea (compound 48)

Yield 60.7%, m.p. 235°–238° C.

NMR (δ, ppm; DMSO-d$_6$) 2.32 (s, 3H), 2.44 (s, 3H), 6.90 (s, 1H), 6.97 (s, 1H), 7.24 (t, 2H), 7.44 (m, 2H), 7.49 (m, 1H), 7.61 (m, 1H), 8.27 (s, 1H), 9.20 (s, 1H).

Example 49

N-[3-(2-Chlorophenyl)-5,7-dimethylbenzofuran-2-yl]-N'-(2,6-dichlorophenyl)urea (compound 49)

Yield 49.2%, m.p. 232°–236° C.

NMR (δ, ppm; DMSO-d$_6$) 2.32 (s, 3H), 2.45 (s, 3H), 6.91 (s, 1H), 6.97 (s, 1H), 7.30 (t, 1H), 7.40–7.56 (m, 5H), 7.60 (dd, 1H), 8.46 (s, 1H), 9.15 (s, 1H).

Example 50

N-[3-(2-Chlorophenyl)-5,7-dimethylbenzofuran-2-yl]-N'-(4-dimethylaminophenyl)urea (compound 50)

Yield 60.9%, m.p. 240°–242° C.

NMR (δ, ppm; DMSO-d$_6$) 2.32 (s, 3H), 2.45 (s, 3H), 2.82 (s, 6H), 6.66 (d, 2H), 6.88 (s, 1H), 6.95 (s, 1H), 7.18 (d, 2H), 7.45 (m, 2H), 7.51 (m, 1H), 7.60 (m, 1H), 8.47 (s, 1H), 8.64 (s, 1H).

Example 51

N-[3-(2-Chlorophenyl)-6,7-dihydro-5H-cyclopenta[f]benzofuran-2-yl]-N'-(2,6-dimethylphenyl)urea (compound 51)

Yield 72.7%, m.p. 247°–250° C.

NMR (δ, ppm; DMSO-d$_6$) 2.05 (m, 2H), 2.11 (s, 6H), 2.88 (t, 2H), 2.95 (t, 2H), 7.04 (s, 3H), 7.09 (s, 1H), 7.43 (m, 3H), 7.51 (m, 1H), 7.60 (m, 1H), 7.88 (s, 1H), 8.91 (br, 1H).

Example 52

N-[3-(2-Chlorophenyl)-6,7-dihydro-5H-cyclopenta[f]benzofuran-2-yl]-N'-(2,6-diethylphenyl)urea (compound 52)

Yield 71.8%, m.p. 264°–266° C.

NMR (δ, ppm; DMSO-d$_6$) 1.08 (t, 6H), 2.04 (m, 2H), 2.47 (q, 4H), 2.87 (t, 2H), 2.95 (t, 2H), 7.07 (t, 3H), 7.14 (t, 1H), 7.43 (m 3H), 7.51 (m, 1H), 7.61 (m, 1H), 7.81 (s, 1H), 8.89 (s, 1H).

Example 53

N-[3-(2-Chlorophenyl)-6,7-dihydro-5H-cyclopenta[f]benzofuran-2-yl]-N'-(2,6-diisopropylphenyl)urea (compound 53)

Yield 67.1%, m.p. 245°–247° C.

NMR (δ, ppm; DMSO-d$_6$) 1.09 (d, 12H), 2.05 (m, 2H), 2.88 (t, 2H), 2.95 (t, 2H), 3.06 (m, 2H), 7.11 (d, 3H), 7.20 (t, 1H), 7.44 (m 3H), 7.51 (m, 1H), 7.61 (d, 1H), 7.81 (s, 1H), 8.86 (s, 1H).

Example 54

N-[3-(2-Chlorophenyl)-6,7-dihydro-5H-cyclopenta[f]benzofuran-2-yl]-N'-(2,4,6-trimethylphenylphenyl)urea (compound 54)

Yield 67.1%, m.p. 245°–247° C.

NMR (δ, ppm; DMSO-d$_6$) 2.04 (m, 2H), 2.06 (s, 6H), 2.20 (s, 3H), 2.87 (t, 2H), 2.95 (t, 2H), 6.84 (s, 2H), 7.09 (s, 1H), 7.43 (m, 3H), 7.50 (m, 1H), 7.60 (m, 1H), 7.78 (s, 1H), 8.90 (br, 1H).

Example 55

N-[3-(2-Chlorophenyl)-6,7-dihydro-5H-cyclopenta[f]benzofuran-2-yl]-N'-(2,4-difluorophenyl)urea (compound 55)

Yield 65.3%, m.p. 208°–209° C.

NMR (δ, ppm; DMSO-$d_6$) 2.06 (m, 2H), 2.88 (t, 2H), 2.96 (t, 2H), 7.03 (dt, 1H), 7.08 (s, 1H), 7.30 (dt, 1H), 7.40–7.55 (m, 4H), 7.63 (m, 1H), 7.92 (m, 1H), 8.69 (s, 1H), 9.07 (s, 1H).

Example 56

N-[3-(2-Chlorophenyl)-6,7-dihydro-5H-cyclopenta[f]benzofuran-2-yl]-N'-(2,4,6-trifluorophenyl)urea (compound 56)

Yield 51.8%, m.p. 244°–247° C.

NMR (δ, ppm; DMSO-$d_6$) 2.05 (m, 2H), 2.88 (t, 2H), 2.96 (t, 2H), 7.10 (s, 1H), 7.24 (t, 2H), 7.40–7.50 (m, 3H), 7.51 (m, 1H), 7.62 (d, 1H), 8.28 (s, 1H), 9.15 (s, 1H).

Example 57

N-[5-Chloro-3-(2-fluorophenyl)benzofuran-2-yl]-N'-(2,6-diethylphenyl)urea (compound 57)

Yield 24.1%, m.p. 237°–238° C.

NMR (δ, ppm; DMSO-$d_6$) 1.10 (t, 6H), 2.49 (q, 4H), 7.06–7.17 (m, 3H), 7.31–7.50 (m, 5H), 7.61–7.66 (m, 2H), 7.99 (s, 1H), 9.19 (s, 1H).

Example 58

N-[5-Chloro-3-(2-fluorophenyl)benzofuran-2-yl]-N'-(2,6-diisopropylphenyl)urea (compound 58)

Yield 27.0%, m.p. 247°–249° C.

NMR (δ, ppm; DMSO-$d_6$) 1.11 (d, 12H), 3.08 (m, 2H), 7.11–7.22 (m, 3H), 7.33–7.50 (m, 5H), 7.61–7.66 (m, 2H), 7.99 (s, 1H), 9.15 (s, 1H).

Example 59

N-[5-Chloro-3-(2-fluorophenyl) benzofuran-2-yl]-N'-(2,4-difluorophenyl)urea (compound 59)

Yield 31.5%, m.p. 265°–266° C.

NMR (δ, ppm; DMSO-$d_6$) 6.98–7.04 (m, 1H), 7.29–7.51 (m, 6H), 7.61–7.67 (m, 2H), 7.82–7.91 (m, 1H), 8.82 (s, 1H), 9.36 (s, 1H).

Example 60

N-[5-Chloro-3-(2-methylphenyl)benzofuran-2-yl]-N'-(2,6-diethylphenyl)urea (compound 60)

To stirred a mixture of 573 mg of 5-chloro-3(2-methylphenyl)benzofuran-2-carboxylic acid and 0.47 cc of diphenylphosphoryl azide in 6 cc of benzene was added dropwise 0.30 cc of triethylamine at room temperature. The resulting mixture was stirred at room temperature for 30 minutes and then heated under reflux for 15 minutes. After cooling, 0.36 cc of 2,6-diethylaniline was added, followed by refluxing for 2 hours. After cooling, water was added to the reaction mixture and was extracted with chloroform. The extract was dried over magnesium sulfate, and distilled to remove the solvent. The crude product thus obtained was purified by a silica gel column chromatography (eluent: chloroform) to obtain 219 mg of compound 60.

Yield 25.3%, m.p. 233°–234° C.

NMR (δ, ppm; DMSO-$d_6$) 1.06 (t, 6H), 2.22 (s, 3H), 2.45 (q, 4H), 7.02–7.20 (m, 4H), 7.29–7.37 (m, 5H), 7.64 (d, 1H), 7.89 (s, 1H), 8.99 (s, 1H).

The compounds described in Examples 61 to 63 were obtained in the same manner as in Example 60.

Example 61

N-[5-Chloro-3-(2-methylphenyl)benzofuran-2-yl]-N'-(2,6-diisopropylphenyl)urea (compound 61)

Yield 21.8%, m.p. 254°–256° C.

NMR (δ, ppm; DMSO-$d_6$) 1.10 (d, 12H), 2.22 (s, 3H), 3.02 (m, 2H), 7.10–7.22 (m, 4H), 7.31–7.38 (m, 5H), 7.64 (d, 1H), 7.88 (s, 1H), 8.94 (s, 1H).

Example 62

N-[5-Chloro-3-(2-methylthiophenyl)benzofuran-2-yl]-N'-(2,6-diethylphenyl)urea (compound 62)

Yield 41.9%, m.p. 208°–210° C.

NMR (δ, ppm; DMSO-$d_6$) 1.08 (t, 6H), 2.41 (s, 3H), 2.48 (q, 4H), 7.05–7.30 (m, 7H), 7.32–7.43 (m, 2H), 7.62 (d, 1H), 7.84 (s, 1H), 8.98 (s, 1H).

Example 63

N-[5-Chloro-3-(2-methylthiophenyl)benzofuran-2-yl]-N'-(2,6-diisopropylphenyl)urea (compound 63)

Yield 43.8%, m.p. 213°–215° C.

NMR (δ, ppm; DMSO-$d_6$) 1.09 (d, 12H), 2.42 (s, 3H), 3.08 (m, 2H), 7.11–7.13 (m, 2H), 7.19–7.36 (m, 5H), 7.44–7.49 (m, 2H), 7.62 (d, 1H), 7.83 (s, 1H), 8.94 (s, 1H).

Example 64

N-[5-Chloro-3-(2-chlorophenyl)-1-benzothiophen-2-yl]-N'-(2,6-dimethylphenyl)urea (compound 64)

To a stirred mixture of 400 mg of 5-chloro-3-(2-chlorophenyl)-1-benzothiophene-2-carboxylic acid and 0.27 cc of diphenylphosphoryl azide in 3 cc of benzene was added dropwise 0.175 cc of triethylamine at room temperature. The resulting mixture was stirred at room temperature for 15 minutes and then heated under reflux for 20 minutes. After cooling, 0.16 cc of 2,6-dimethylaniline was added and the resulting mixture was stirred at room temperature for 30 minutes, followed by refluxing for 1 hour. After cooling, water was added to the reaction mixture and was extracted with chloroform. The extract was dried over magnesium sulfate and distilled to remove the solvent. The crude product thus obtained was purified by a silica gel column chromatography (eluent: chloroform/hexane=7/3) to obtain 175 mg of compound 64.

Yield 32.2%, m.p. 203°–204° C.

NMR (δ, ppm; DMSO-$d_6$) 2.27 (s, 6H), 6.89 (d, 1H), 7.07 (s, 3H), 7.20 (dd, 1H), 7.50–7.61 (m, 3H), 7.71–7.79 (m, 1H), 7.87 (d, 1H), 8.31 (s, 1H), 9.10 (s, 1H).

The compounds described in Examples 65 to 86 were obtained in the same manner as in Example 64.

Example 65

N-[5-Chloro-3-(2-chlorophenyl)-1-benzothiophen-2-yl]-N'-(2,6-diethylphenyl)urea (compound 65)

Yield 39.0%, m.p. 145°–147° C.

NMR (δ, ppm; DMSO-$d_6$) 1.11 (t, 6H), 2.52 (q, 4H), 6.91 (d, 1H), 7.10 (s, 1H), 7.13 (s, 1H), 7.17 (s, 1H), 7.21 (dd, 1H), 7.54–7.79 (m, 3H), 7.87 (d, 1H), 8.25 (s, 1H), 9.12 (s, 1H).

Example 66

N-[5-Chloro-3-(2-chlorophenyl)-1-benzothiophen-2-yl]-N'-(2,6-diisopropylphenyl)urea (compound 66)

Yield 29.8%, m.p. 126°–127° C.

NMR (δ, ppm; DMSO-d$_6$) 1.11 (d, 12H), 3.05 (m, 2H), 6.90 (d, 1H), 7.13 (d, 1H), 7.17 (s, 1H), 7.22 (s, 1H), 7.27 (d, 1H), 7.53–7.61 (m, 3H), 7.71–7.79 (m, 1H), 7.87 (d, 1H), 8.20 (s, 1H), 9.10 (s, 1H).

Example 67

N-[5-Chloro-3-(2-chlorophenyl)-1-benzothiophen-2-yl]-N'-(2-isopropyl-6-methylphenyl)urea (compound Yield 28.9%, m.p. 219°–220° C.

NMR (δ, ppm ; DMSO-d$_6$) 1.10 (d, 6H), 2.16 (s, 3H), 3.07 (m, 1H), 6.90 (d, 1H), 7.05–7.25 (m, 4H), 7.50–7.62 (m, 3H), 7.71–7.79 (m, 1H), 7.87 (d, 1H), 8.26 (s, 1H), 9.12 (s, 1H).

Example 68

N-[5-Chloro-3-(2-chlorophenyl)-1-benzothiophen-2-yl]-N'-(2,4-difluorophenyl)urea (compound 68)

Yield 39.1%, m.p. 232°–233° C.

NMR (δ, ppm; CDCl$_3$) 6.75–6.88 (m, 2H), 7.11 (d, 1H), 7.21 (dd, 1H), 7.36–7.41 (m, 3H), 7.52–7.56 (m, 1H), 7.59 (s, 1H), 7.68 (d, 1H), 7.82 (s, 1H), 7.92–8.01 (m, 1H).

Example 69

N-[5-Chloro-3-(2-chlorophenyl )-1-benzothiophen-2-yl]-N'-(2,6-difluorophenyl)urea (compound 69)

Yield 48.2%, m.p. 239°–240° C.

NMR (δ, ppm; CDCl$_3$) 6.86 (t, 2H), 7.00 (d, 1H), 7.09 (dd, 1H), 7.01–7.13 (m, 1H), 7.36–7.42 (m, 3H), 7.53–7.57 (m, 1H), 7.59 (d, 1H), 8.37 (s, 1H), 8.77 (s, 1H).

Example 70

N-[5-Chloro-3-(2-chlorophenyl )-1-benzothiophen- 2-yl ]-N'-(2,4,6-trifluorophenyl)urea (compound Yield 37.4%, m.p. 230°–231° C.

NMR (δ, ppm; CDCl$_3$) 6.67 (t, 2H), 7.12 (d, 1H), 7.20 (dd, 2H), 7.28–7.36 (m, 4H), 7.65 (d, 1H), 7.95 (s, 1H).

Example 71

N-[5-Chloro-3-(2-chlorophenyl)-1-benzothiophen-2-yl]-N'-(2,6-dichlorophenyl)urea (compound 71)

Yield 31.8%, m.p. 186°–187° C.

NMR (δ, ppm; DMSO-d$_6$) 6.91 (d, 1H), 7.22 (dd, 1H), 7.29–7.38 (m, 1H), 7.50–7.65 (m, 5H), 7.71–7.81 (m, 1H), 7.90 (d, 1H), 8.76 (s, 1H), 9.28 (s, 1H).

Example 72

N-[3-(2-Chlorophenyl)-5-methyl-1-benzothiophen-2-yl]-N'-(2,6-diethylphenyl)urea (compound 72)

Yield 81.3%, m.p. 125°–126° C.

NMR (δ, ppm; DMSO-d$_6$) 1.11 (t, 6H), 2.30 (s, 3H), 2.53 (q, 4H), 6.80 (s, 1H), 7.02 (d, 1H), 7.08–7.22 (m, 3H), 7.49–7.12 (m, 3H), 7.70 (d, 1H), 7.72–7.80 (m, 1H), 8.21 (s, 1H), 8.93 (s, 1H).

Example 73

N-[3-(2-Chlorophenyl)-5-methyl-1-benzothiophen- 2-yl]-N'-(2,6-diisopropylphenyl)urea (compound 73)

Yield 79.3%, m.p. 193°–194° C.

NMR (δ, ppm; DMSO-d$_6$) 1.10 (d, 12H), 2.30 (s, 3H), 3.06 (m, 2H), 6.80 (s, 1H), 7.02 (d, 1H), 7.17 (d, 2H), 7.25 (d, 1H), 7.50–7.75 (m, 3H), 7.69 (d, 1H), 7.73–7.80 (m, 1H), 8.17 (s, 1H), 8.92 (s, 1H).

Example 74

N-[3-(2-Chlorophenyl)-5-methyl-1-benzothiophen-2-yl]-N'-(2-isopropyl-6-methylphenyl)urea (compound Yield 68.8%, m.p. 203°–205° C.

NMR (δ, ppm; DMSO-d$_6$) 1.12 (d, 6H), 2.17 (s, 3H), 2.30 (s, 3H), 3.08 (m, 1H), 6.79 (s, 1H), 7.02 (d, 1H), 7.06–7.18 (m, 3H), 7.50–7.62 (m, 3H), 7.70 (d, 1H), 7.72–7.80 (m, 1H), 8.22 (s, 1H), 8.94 (s, 1H).

Example 75

N-[3-(2-Chlorophenyl)-5-methyl-1-benzothiophen-2-yl ]-N'-(2,4-difluorophenyl)urea (compound 75)

Yield 79.3%, m.p. 186°–187° C.

NMR (δ, ppm; CDCl$_3$) 2.30 (s, 3H), 6.72–6.88 (m, 2H), 6.97–7.07 (m, 2H), 7.13 (dd, 1H), 7.18 (s, 1H), 7.33–7.42 (m, 3H), 7.47–7.57 (m, 1H), 7.69 (d, 1H), 7.80–7.95 (m, 1H).

Example 76

N-[3-(2-Chlorophenyl)-5-isopropyl-1-benzothiophen- 2-yl]-N'-(2,6-diethylphenyl)urea (compound 76) Yield 69.7%, m.p. 135°–137° C.

NMR (δ, ppm; DMSO-d$_6$) 1.11 (t, 6H), 1.16 (d, 6H), 2.53 (q, 4H), 2.87 (m, 1H), 6.85 (s, 1H), 7.07–7.22 (m, 4H), 7.50–7.64 (m, 3H), 7.70–7.80 (m, 2H), 8.21 (s, 1H), 8.92 (s, 1H).

Example 77

N-[3-(2-chlorophenyl)-5-isopropyl-1-benzothiophen-2-yl]-N'-(2,6-diisopropylphenyl)urea (compound 77)

Yield 54.6%, m.p. 147°–149° C.

NMR (δ, ppm; DMSO-d$_6$) 1.05–1.25 (m, 18H), 2.86 (m, 1H), 3.08 (m, 2H), 6.85 (s, 1H), 7.08–7.30 (m, 4H), 7.52–7.65 (m, 3H), 7.70–7.81 (m, 2H), 8.18 (s, 1H), 8.91 (s, 1H).

Example 78

N-[3-(2-Chlorophenyl )-5-isopropyl-1-benzothiophen-2-yl ]-N'-(2,4-difluorophenyl)urea (compound 78)

Yield 67.5%, m.p. 221°–222° C.

NMR (δ, ppm; DMSO-d$_6$) 1.16 (d, 6H), 2.87 (m, 1H), 6.83 (s, 1H), 7.08 (dt, 1H), 7.15 (d, 1H), 7.33 (dt, 1H), 7.45–7.65 (m, 3H), 7.73–7.81 (m, 2H), 8.10–8.21 (m, 1H), 9.13 (s, 1H), 9.26 (s, 1H).

Example 79

N-[3-(2-Chlorophenyl)-5,6-dimethyl-1-benzothiophen-2-yl]-N'-(2,4-dimethylphenyl)urea (compound 79)

Yield 78.3%, m.p. 145°–147° C.

NMR (δ, ppm; DMSO-d$_6$) 2.14 (s, 3H), 2.20 (s, 3H), 2.23 (s, 3H), 2.29 (s, 3H), 6.74 (s, 1H), 6.65–7.00 (m, 2H), 7.45–7.75 (m, 6H), 8.36 (s, 1H), 9.50 (s, 1H).

Example 80

N-[3-(2-Chlorophenyl)-5,6-dimethyl-1-benzothiophen-2-yl]-N'-(2,6-diethylphenyl)urea (compound 80)

Yield 97.3%, m.p. 205°–206° C.

NMR (δ, ppm; DMSO-d$_6$) 1.10 (t, 6H), 2.22 (s, 3H), 2.30 (s, 3H), 2.53 (q, 4H), 6.80 (s, 1H), 7.08–7.26 (m, 3H), 7.45–7.65 (m, 4H), 7.70–7.83 (m, 1H), 8.20 (s, 1H ), 8.88 (s, 1H ).

Example 81

N-(3-(2-Chlorophenyl)-5,6-dimethyl-1-benzothiophen-2-yl]-N'-(2,6-diisopropylphenyl)urea (compound
Yield 88.4%, m.p. 205°–207° C.
NMR (δ, ppm; DMSO-d$_6$) 1.10 (d, 12H), 2.21 (s, 3H), 2.29 (s, 3H), 3.09 (m, 2H), 6.80 (s, 1H), 7.13–7.32 (m, 3H), 7.50–7.63 (m, 4H), 7.72–7.80 (m, 1H), 8.15 (s, 1H), 8.87 (s, 1H).

Example 82

N- [3-(2-Chlorophenyl)-5,6-dimethyl-1-benzothiophen-2-yl]-N'-(2-isopropyl-6-methylphenyl)urea (compound 82)
Yield 94.3%, m.p. 205°–206° C.
NMR (δ, ppm; DMSO-d$_6$) 1.13 (d, 6H), 2.16 (s, 3H), 2.20 (s, 3H), 2.30 (s, 3H), 3.10 (m, 1H), 6.79 (s, 1H), 7.05–7.20 (m, 3H), 7.45–7.63 (m, 4H), 7.60–7.72 (m, 1H){), 8.21 (s, 1H), 8.89 (s, 1H).

Example 83

N-[3-(2-Chlorophenyl )-5,6-dimethyl-1-benzothiophen-2-yl]-N'-(2-dimethylamino-6-methylphenyl)urea (compound 83)
Yield 82.8%, m.p. 204°–206° C.
NMR (δ, ppm; DMSO-$_6$) 2.15 (s, 3H), 2.20 (s, 3H), 2.29 (s, 3H), 2.56 (s, 6H), 6.76 (s, 1H), 6.89 (d, 2H), 7.07 (t, 1H), 7.43–7.48 (m, 1H), 7.53–7.58 (m, 3H), 7.69–7.73 (m, 1H), 8.24 (s, 1H), 9.09 (s, 1H).

Example 84

N-[3-(2-Chlorophenyl)-5,6-dimethyl-1-benzothiophen-2-yl]-N'-(2,4-difluorophenyl)urea (compound 84)
Yield 86.0%, m.p. 147°–150° C.
NMR (δ, ppm; CDCl$_3$) 2.25 (s, 3H), 2.33 (s, 3H), 6.70–6.92 (m, 3H), 7.37–7.47 (m, 3H), 7.52–7.63 (m, 2H), 8.24 (dt, 1H), 8.56 (s, 1H), 8.70 (s, 1H).

Example 85

N-[3-(2-Chlorophenyl)-5,6-dimethyl-1-benzothiophen-2-yl]-N'-(2-fluoro-4-methylphenyl)urea (compound 85)
Yield 61.2%, m.p. 207°–208° C.
NMR (δ, ppm; DMSO-$_6$) 2.21 (s, 3H), 2.27 (s, 3H), 2.30 (s, 3H), 6.77 (s, 1H), 6.95–7.08 (m, 2H), 7.45 (m, 5H), 8.02 (t, 1H), 9.02 (s, 1H), 9.18 (s, 1H).

Example 86

N-[3-(2-Chlorophenyl)-5,6-dimethyl-1-benzothiophen-2-yl]-N'-(2,4,6-trimethoxyphenyl)urea (compound 86)
Yield 80.5%, m.p. 215°–216° C.
NMR (δ, ppm; CDCl$_3$) 2.27 (s, 3H), 2.35 (s, 3H), 3.61 (s, 6H), 3.81 (s, 3H), 5.81 (s, 1H), 6.02 (s, 2H), 6.92 (s, 1H), 7.22–7.37 (m, 4H), 7.42–7.49 (m, 1H), 7.54 (s, 1H).

Example 87

N-[3-(2-Chlorophenyl)-6,7-dihydro-5H-cyclopenta[f][1]benzothiophen-2-yl]-N'-(2,6-dimethylphenyl)urea (compound 87)

To a stirred mixture of 400 mg of 3-(2-chlorophenyl)-6,7-dihydro-5H-cyclopenta[f][1]benzothiophene-2-carboxylic acid and 0.27 cc of diphenylphosphoryl azide in 5 cc of benzene was added dropwise 0.175 cc of triethylamine at room temperature. The resulting mixture was stirred at room temperature for 15 minutes and then heated under reflux for 30 minutes. After cooling, 0.155 cc of 2,6-dimethylaniline was added, followed by refluxing for 2 hours. After cooling, water was added to the reaction mixture and the desired compound was extracted with chloroform. The extract was dried over magnesium sulfate, and distilled to remove the solvent. The crude product thus obtained was purified by a silica gel column chromatography (eluent: ethyl acetate/hexane=15/85) to obtain 454 mg of compound 87.
Yield 84.6%, m.p. 236°–237° C.
NMR (δ, ppm; DMSO-$_6$) 2.05 (m, 2H), 2.18 (s, 6H), 2.85 (t, 2H), 2.94 (t, 2H), 6.90–7.50 (m, 4H), 7.20–7.50 (m, 4H), 7.55 (s, 1H).

The compounds described in Examples 88 to 101 were obtained in the same manner as in Example 87.

Example 88

N-[3-(2-Chlorophenyl)-6,7-dihydro-5H-cyclopenta[f][1]benzothiophen-2-yl]-N'-(2,6-diethylphenyl)urea (compound 88)
Yield 98.5%, m.p. 205°–206° C.
NMR (δ, ppm; DMSO-$_6$) 1.11 (t, 6H), 2.01 (m, 2H), 2.53 (q, 4H), 2.82 (t, 2H), 2.91 (t, 2H), 6.83 (s, 1H), 7.08–7.25 (m, 3H), 7.45–7.80 (m, 5H), 8.17 (s, 1H), 8.86 (s, 1H).

Example 89

N- [3-(2-Chlorophenyl)-6,7-dihydro-5H-cyclopenta[f][1]benzothiophen-2-yl]-N'-(2,6-diisopropylphenyl)urea (compound 89)
Yield 72.9%, m.p. 213°–214° C.
NMR (δ, ppm; DMSO-$_6$) 1.10 (d, 12H), 2.00 (m, 2H), 2.81 (t, 2H), 2.88 (t, 2H), 3.07 (m, 2H), 6.81 (s, 1H), 7.12–7.30 (m, 3H), 7.48–7.60 (m, 3H), 7.63 (s, 1H), 7.72–7.78 (m, 1H), 8.12 (s, 1H), 8.83 (s, 1H).

Example 90

N-[3-(2-Chlorophenyl)-6,7-dihydro-5H-cyclopenta[f][1]benzothiophen-2-yl]-N'-(2-isopropyl-6-methylphenyl)urea (compound 90)
Yield 79.1%, m.p. 200°–202° C.
NMR (δ, ppm; DMSO-$_6$) 1.13 (d, 6H), 2.01 (m, 2H), 2.16 (s, 3H), 2.82 (t, 2H), 2.91 (t, 2H), 3.08 (m, 1H), 6.83 (s, 1H), 7.05–7.20 (m, 3H), 7.45–7.75 (m, 5H), 8.19 (s, 1H), 8.88 (s, 1H).

Example 91

N- [3-(2-Chlorophenyl)-6,7-dihydro-5H-cyclopenta[f][1]-benzothiophen-2-yl [-N'-(2 -dimethylamino-6-methylphenyl)urea (compound 91)
Yield 79.5%, m.p. 192°–194° C.
NMR (δ, ppm; DMSO-$_6$) 2.01 (m, 2H), 2.15 (s, 3H), 2.56 (s, 6H), 2.82 (t, 2H), 2.91 (t, 2H), 6.81 (s, 1H), 6.88 (d, 2H), 7.07 (t, 1H), 7.44–7.72 (m, 5H), 8.24 (d, 20 1H), 9.08 (s, 1H).

Example 92

N-(3-(2-Chlorophenyl)-6,7-dihydro-5H-cyclopenta[f][1]benzothiophen-2-yl]-N'-(2,4-difluorophenyl)urea (compound 92)
Yield 80.6%, m.p. 129°–130° C.
NMR (δ, ppm; CDCl$_3$) 2.01 (m, 2H), 2.90 (t, 2H), 2.99 (t, 2H), 6.72–6.85 (m, 2H), 7.03 (s, 1H), 7.25–7.55 (m, 6H), 7.62 (s, 1H), 7.87–7.97 (m, 1H).

Example 93

N-[3-(2-Chlorophenyl)-6,7-dihydro-5H-cyclopenta[f][1]benzothiophen-2-yl]-N'-(2,6-difluorophenyl)urea (compound 93)

Yield 75.2%, m.p. 252°–253° C.

NMR (δ, ppm; CDCl₃) 2.01 (m, 2H), 2.82 (t, 2H), 2.90 (t, 2H), 6.82–6.92 (m, 3H), 7.00–7.11 (m, 1H), 7.32–7.41 (m, 3H), 7.51–7.57 (m, 2H), 8.28 (s, 1H), 8.56 (s, 1H).

Example 94

N-[3-(2-Chlorophenyl)-6,7-dihydro-5H-cyclopenta[f][1]benzothiophen-2-yl]-N'-(2,4,6-trifluorophenyl)urea (compound 94)

Yield 62.3%, m.p. 235°–236° C.

NMR (δ, ppm; CDCl₃) 2.01 (m, 2H), 2.90 (t, 2H), 3.00 (t, 2H), 6.50 (s, 1H), 6.65 (t, 2H), 7.05 (s, 2H), 7.35–7.42 (m, 3H), 7.48–7.53 (m, 1H), 7.61 (s, 1H).

Example 95

N-[3-(2-Chlorophenyl)-6,7-dihydro-5H-cyclopenta[f][1]benzothiophen-2-yl]-N'-(2,6-dichlorophenyl)urea (compound 95)

Yield 72.2%, m.p. 158°–159° C.

NMR (δ, ppm; CDCl₃) 2.10 (m, 2H), 2.90 (t, 2H), 2.99 (t, 2H), 6.65 (s, 1H), 6.87 (s, 1H), 7.07 (t, 2H), 7.25–7.53 (m, 6H), 7.60 (s, 1H).

Example 96

N-[3-(2-Chlorophenyl)-5,6,7,8-tetrahydronaphthono[2,3-b]thiophen-2-yl]-N'-(2,6-diethylphenyl)urea (compound 96)

Yield 93.8%, m.p. 178°–180° C.

NMR (δ, ppm; DMSO-₆) 1.12 (t, 6H), 1.71 (m, 4H), 2.53 (q, 4H), 2.72 (t, 2H), 2.82 (t, 2H), 6.68 (s, 1H), 7.06–7.25 (m, 3H), 7.45–7.60 (m, 4H), 7.70–7.80 (m, 1H), 8.18 (s, 1H), 8.87 (s, 1H).

Example 97

N-[3-(2-Chlorophenyl)-5,6,7,8-tetrahydronaphtho[2,3-b]thiophen-2-yl]-N'-(2,6-diisopropylphenyl)urea (compound 97)

Yield 81.2%, m.p. 214°–216° C.

NMR (δ, ppm; DMSO-₆) 1.10 (d, 12H), 1.71 (m, 4H), 2.72 (t, 2H), 2.82 (t, 2H), 3.07 (m, 2H), 6.68 (s, 1H), 7.12–7.33 (m, 3H), 7.46–7.60 (m, 4H), 7.70–7.78 (m, 1H), 8.15 (s, 1H), 8.86 (s, 1H).

Example 98

N-[3-(2-Chlorophenyl)-5,6,7,8-tetrahydronaphtho[2,3-b]thiophen-2-yl]-N'-(2-isopropyl-6-methylphenyl)urea (compound 98)

Yield 95.8%, m.p. 138°–140° C.

NMR (δ, ppm; DMSO-₆) 1.13 (d, 6H), 1.71 (m, 4H), 2.17 (s, 2H) 2.71 (t, 2H), 2.81 (t, 2H), 3.09 (m, 1H), 6.68 (s, 1H), 7.02–7.18 (m, 3H), 7.45–7.60 (m, 4H), 7.70–7.78 (m, 1H), 8.20 (s, 1H), 8.88 (s, 1H).

Example 99

N-[3-(2-Chlorophenyl)-5,6,7,8-tetrahydronaphtho[2,3-b]thiophen-2-yl]-N'-(2,4-difluorophenyl)urea (compound 99)

Yield 71.6%, m.p. 134°–135° C.

NMR (δ, ppm; CDCl₃) 1.80 (m, 4H), 2.78 (t, 2H), 2.90 (t, 2H), 6.72–6.93 (m, 3H), 7.12 (br, 2H), 7.33–7.58 (m, 5H), 7.88–8.01 (m, 1H).

Example 100

N-[3-(2,4-Dichlorophenyl)-5-nitro-1-benzothiophen-2-yl]-N'-(2,6-diisopropylphenyl)urea (compound 100)

Yield 48.9%, m.p. 145°–146° C.

NMR (δ, ppm; DMSO-₆) 1.10 (d, 12H), 3.07 (m, 2H), 7.17–7.35 (m, 3H), 7.64–7.82 (m, 3H), 8.00–8.08 (m, 2H), 8.14–8.22 (m, 2H), 9.37 (s, 1H).

Example 101

N-[3-(2,4-Dichlorophenyl)-5-nitro-1-benzothiophen-2-yl]-N'-(2,4-difluorophenyl)urea (compound 101)

Yield 19.3%, m.p. 261°–263° C.

NMR (δ, ppm; DMSO-₆) 7.10 (t, 1H), 7.35 (t, 1H), 7.60–7.82 (m, 3H), 7.98–8.25 (m, 4H), 9.10 (s, 1H), 9.60 (d, 1H).

Example 102

N-[3-(2-Chlorophenyl)-5,6-dimethoxy-1-benzothiophen-2-yl]-N'-(2,6-diethylphenyl)urea (compound 102)

To a stirred mixture of 500 mg of 3-(2-chlorophenyl)-5,6-dimethoxy-1-benzothiophen-2-carboxylic acid and 0.32 cc of diphenylphosphoryl azide in 5 cc of benzene was added dropwise 0.15 cc of triethylamine at room temperature. The resulting mixture was stirred at room temperature for 15 minutes and then heated under reflux for 30 minutes. After cooling, 0.245 cc of 2,6-diethylaniline was added, followed by refluxing for 2 hours. After cooling, water was added to the reaction mixture and extracted with ethyl acetate. The extract was dried over magnesium sulfate, and distilled to remove the solvent. The crude product thus obtained was purified by a silica gel column chromatography (eluent: ethyl acetate/hexane=3/7) to obtain 554 mg of compound 102.

Yield 78.3%, m.p. 229°–231° C.

NMR (δ, ppm; DMSO-₆) 1.11 (t, 6H), 2.53 (q, 4H), 3.63 (s, 3H), 3.80 (s, 3H), 6.49 (s, 1H), 7.06–7.22 (m, 3H), 7.45 (s, 1H), 7.48 (m, 3H), 7.70–7.78 (m, 1H), 8.14 (s, 1H), 8.80 (s, 1H).

The compounds described in Examples 103 to 119 were obtained in the same manner as in Example 102.

Example 103

N-[3-(2-Chlorophenyl)-5,6-dimethoxy-1-benzothiophen-2-yl]-N'-(2,6-diisopropylphenyl)urea (compound 103)

Yield 96.3%, m.p. 135°–137° C.

NMR (δ, ppm; DMSO-₆) 1.10 (d, 12H), 3.09 (m, 2H), 3.64 (s, 3H), 3.82 (s, 3H), 6.50 (s, 1H), 7.12–7.32 (m, 3H), 7.45 (s, 1H), 7.52–7.63 (m, 3H), 7.73–7.80 (m, 1H), 8.12 (s, 1H), 8.80 (s, 1H).

Example 104

N-[3-(2-Chlorophenyl)-5,6-dimethoxy-1-benzothiophen-2-yl]-N'-(2-isopropyl-6-methylphenyl)urea (compound 104)

Yield 83.2%, m.p. 134°–137° C.

NMR (δ, ppm; DMSO-₆) 1.13 (d, 6H), 2.17 (s, 3H), 3.09 (m, 1H), 3.63 (s, 3H), 3.80 (s, 3H), 6.49 (s, 1H), 7.03–7.18 (m, 3H), 7.45 (s, 1H), 7.48–7.60 (m, 3H), 7.70–7.78 (m, 1H), 8.16 (s, 1H), 8.82 (s, 1H).

Example 105

N-[3-(2-Chlorophenyl)-5,6-dimethoxy-1-benzothiophen-2-yl]-N'-(2,4-difluorophenyl)urea (compound 105)

Yield 85.4%, m.p. 186°–187° C.

NMR (δ, ppm; DMSO-$_6$) 3.62 (s, 3H), 3.82 (s, 3H), 6.46 (s, 1H), 7.07 (dt, 1H), 7.32 (dt, 1H), 7.45–7.62 (m, 4H), 7.70–7.78 (m, 1H), 8.08–8.20 (m, 1H), 9.06 (s, 1H), 9.15 (d, 1H).

Example 106

N-[3-(2,4-Dichlorophenyl)-6,7-dihydro-5H-cyclopenta[f][1]benzothiophen-2-yl]-N'-(2,6-diisopropylphenyl)urea (compound 106)

Yield 41.4%, m.p. 220°–222° C.

NMR (δ, ppm; DMSO-$_6$) 1.10 (d, 12H), 2.02 (m, 2H), 2.83 (t, 2H), 2.91 (t, 2H), 3.07 (m, 2H), 6.87 (s, 1H), 7.16 (d, 2H), 7.22–7.30 (m, 1H), 7.54 (d, 1H), 7.60–7.68 (m, 2H), 7.92 (s, 1H), 8.04 (s, 1H), 8.90 (s, 1H).

Example 107

N-[3-(2,4-Dichlorophenyl)-6,7-dihydro-5H-cyclopenta[f][1]benzothiophen-2-yl]-N'-(2,4-difluorophenyl)urea (compound 107)

Yield 57.1%, m.p. 201°–202° C.

NMR (δ, ppm; DMSO-$_6$) 2.02 (m, 2H), 2.83 (t, 2H), 2.90 (t, 2H), 6.85 (s, 1H), 7.07 (td, 1H), 7.33 (td, 1H), 7.45–7.73 (m, 3H), 7.91 (s, 1H), 8.07–8.20 (m, 1H), 8.99 (s, 1H), 9.21 (s, 1H).

Example 108

N-(2,6-Diethylphenyl)-N'-[3-(2-fluorophenyl)-6,7-dihydro-5H-cyclopenta[f][1]benzothiophen-2-yl]urea (compound 108)

Yield 78.4%, m.p. 223°–225° C.

NMR (δ, ppm; DMSO-$_6$) 1.11 (t, 6H), 2.02 (m, 2H), 2.51 (q, 4H), 2.84 (t, 2H), 2.91 (t, 2H), 6.98 (s, 1H), 7.10–7.20 (m, 3H), 7.40–7.60 (m, 4H), 7.64 (s, 1H), 8.20 (s, 1H), 8.97 (s, 1H).

Example 109

N-(2,6-Diethylphenyl)-N'-[3-(2-methylphenyl)-6,7-dihydro-5H-cyclopenta[f][1]benzothiophen-2-yl]urea (compound 109)

Yield 70.3%, m.p. 188°–191° C.

NMR (δ, ppm; DMSO-d$_6$) 1.09 (t, 6H), 2.01 (m, 2H), 2.13 (s, 3H), 2.53 (q, 4H), 2.82 (t, 2H), 2.91 (t, 2H), 6.80 (s, 1H), 7.05–7.55 (m, 7H), 7.64 (s, 1H), 8.25 (s, 1H), 8.71 (s, 1H).

Example 110

N-(2,6-Diisopropylphenyl)-N'-[3-(2-methylphenyl)-6,7-dihydro-5H-cyclopenta[f][1]benzothiophen-2-yl]urea (compound 110)

Yield 83.7%, m.p. 197°–199° C.

NMR (δ, ppm; DMSO-$_6$) 1.13 (d, 12H), 2.01 (m, 2H), 2.12 (s, 3H), 2.82 (t, 2H), 2.91 (t, 2H), 3.08 (m, 2H), 6.80 (s, 1H), 7.11–7.52 (m, 7H), 8.19 (s, 1H), 8.68 (s, 1H).

Example 111

N-(2-Isopropyl-6-methylphenyl)-N'-[3-(2methylphenyl)-6,7-dihydro-5H-cyclopenta[f][1]benzothiophen-2-yl]urea (compound 111)

Yield 87.8%, m.p. 210°–213° C.

NMR (δ, ppm; DMSO-$_6$) 1.12 (d, 6H), 2.01 (m, 2H), 2.12 (s, 3H), 2.16 (s, 3H), 2.81 (t, 2H), 2.91 (t, 2H), 3.03–3.15 (m, 1H), 6.79 (s, 1H), 7.03–7.52 (m, 7H), 7.63 (s, 1H), 8.24 (s, 1H), 8.71 (s, 1H).

Example 112

N-(2,4-Difluorophenyl)-N'-[3-(2-methylphenyl)-6,7-dihydro-5H-cyclopenta[f][1]benzothiophen-2-yl]-urea (compound 112)

Yield 89.0%, m.p. 185°–186° C.

NMR (δ, ppm; CDCl$_3$) 2.10 (m, 2H), 2.12 (s, 3H), 2.88 (t, 2H), 2.99 (t, 2H), 6.71–6.86 (m, 2H), 6.98 (s, 1H), 7.03 (d, 1H), 7.15–7.35 (m, 5H), 7.63 (s, 1H), 7.80–7.93 (s, 1H).

Example 113

N-(2,6-Diethylphenyl)-N'-[3-(2-trifluoromethylphenyl)-6,7-dihydro-5H-cyclopenta[f][1]-benzothiophen-2-yl]urea (compound 113)

Yield 81.5%, m.p. 202°–204° C.

NMR (δ, ppm; DMSO-$_6$) 1.08 (t, 6H), 2.00 (m, 2H), 2.50 (q, 4H), 2.79 (t, 2H), 2.90 (t, 2H), 6.64 (s, 1H), 7.05–7.20 (m, 3H), 7.50 (d, 1H), 7.62 (s, 1H), 7.77 (t, 1H), 7.88 (t, 1H), 8.00 (d, 1H), 8.06 (s, 1H), 8.71 (s, 1H).

Example 114

N-(2,6-Diisopropylphenyl)-N'-[3-(2-trifluoromethylphenyl)-6,7-dihydro-5H-cyclopenta[f][1]-benzothiophen-2-yl]urea (compound 114)

Yield 74.7%, m.p. 217°–220° C.

NMR (δ, ppm; DMSO-$_6$) 1.10 (d, 12H), 2.00 (m, 2H), 2.79 (t, 2H), 2.91 (t, 2H), 3.05 (m, 2H), 6.64 (s, 1H), 7.10–7.28 (m, 3H), 7.50 (d, 1H), 7.61 (s, 1H), 7.77 (t, 1H), 7.89 (t, 1H), 7.95–8.05 (m, 2H), 8.68 (s, 1H).

Example 115

N-(2,4-Difluorophenyl)-N'-[3-(2-trifluoromethylphenyl)-6,7-dihydro-5H-cyclopenta[f][1]benzothiophen-2-yl]urea (compound 115)

Yield 79.2%, m.p. 132°–135° C.

NMR (δ, ppm; DMSO-$_6$) 2.00 (m, 2H), 2.79 (t, 2H), 2.91 (t, 2H), 6.64 (s, 1H), 7.06 (td, 1H), 7.30 (td, 1H), 7.46 (d, 1H), 7.66 (s, 1H), 7.78 (t, 1H), 7.87 (t, 1H), 8.01 (d, 1H), 8.08–8.18 (m, 1H), 8.98 (s, 1H), 9.06 (s, 1H).

Example 116

N-(2,6-Diethylphenyl)-N'-[3-(2-methoxyphenyl)-6,7-dihydro-5H-cyclopenta[f][1]benzothiophen-2-yl]urea (compound 116)

Yield 89.0%, m.p. 205°–206° C.

NMR (δ, ppm; DMSO-$_6$) 1.11 (t, 6H), 2.01 (m, 2H), 2.53 (q, 4H), 2.81 (t, 2H), 2.90 (t, 2H), 3.80 (s, 3H), 6.97 (s, 1H), 7.10–7.50 (m, 7H), 7.59 (s, 1H), 8.33 (s, 1H), 8.60 (s, 1H).

Example 117

N-(2,6-Diethylphenyl)-N'-[3-(2-methylphenyl)-5,6,7,8-tetrahydronaphtho[2,3-b]thiophen-2-yl]urea (compound 117)

Yield 81.5%, m.p. 202°–204° C.

NMR (δ, ppm; DMSO-$_6$) 1.10 (t, 6H), 1.72 (m, 4H), 2.12 (s, 3H), 2.52 (q, 4H), 2.69 (t, 2H), 2.81 (t, 2H), 6.66 (s, 1H), 7.05–7.53 (m, 8H), 8.24 (s, 1H), 8.69 (s, 1s).

Example 118

N-(2,6-Diisopropylphenyl)-N'-[3-(2-methylphenyl)-5,6,7,8-tetrahydronaphtho[2,3-b]thiophen-2-yl]urea (compound 118)

Yield 74.7%, m.p. 217°–220° C.

NMR (δ, ppm; DMSO-d$_6$) 1.10 (d, 12H), 1.72 (m, 4H), 2.12 (s, 3H), 2.69 (t, 2H), 2.81 (t, 2H), 3.06 (m, 2H), 6.66

(s, 1H), 7.10–7.53 (m, 8H), 8.20 (s, 1H), 8.68 (s, 1H).

Example 119

N-(2,4-Difluorophenyl)-N'-[3-(2-methylphenyl)5,6,7,8-tetrahydronaphtho[2,3-b]thiophen-2-yl]urea (compound 119)
 Yield 79.3%, m.p. 132°–135° C.
 NMR (δ, ppm; DMSO-$_6$) 1.72 (m, 4H), 2.07 (s, 3H), 2.69 (t, 2H), 2.82 (t, 2H), 6.63 (s, 1H), 7.06 (td, 1H), 7.31–7.50 (m, 5H), 7.52 (s, 1H), 8.08–8.20 (m, 1H), 9.07 (s, 1H), 9.15 (s, 1H).

Example 120

N-(2,4-Difluorophenyl)-N'-[3-phenyl-1-(p-toluenesulfonyl)-3-phenylindole-2-yl]urea (compound 120)
 To a stirred mixture of 1.05 g of 1-(p-toluenesulfonyl)-3-phenylindole-3-carboxylic acid and 0.60 cc of diphenylphosphoryl azide in 10 cc of benzene was added dropwise 0.39 cc of triethylamine at room temperature. The resulting mixture was stirred at room temperature for 15 minutes and then heated under reflux for 30 minutes. After cooling, 0.285 cc of 2,4-difluoroaniline was added and then stirred at room temperature for 30 minutes, followed by refluxing for 2 hours. After cooling, water was added to the reaction mixture and extracted with ethyl acetate. The extract was dried over magnesium sulfate, and distilled to remove the solvent. The crude product thus obtained was purified by a silica gel column chromatography (eluent: ethyl acetate/hexane=1/3) to obtain 780 mg of compound 120. Yield 55.8%, m.p. 244°–246° C.
 NMR (δ, ppm; DMSO-$_6$) 2.28 (s, 3H), 6.94–7.08 (m, 1H), 7.22–7.57 (m, 11H), 7.77–7.91 (m, 3H), 8.08 (d, 1H), 8.72 (s, 2H).

The compounds described in Examples 121 to 125 were obtained in the same manner as in Example 120.

Example 121

N-[3-(2-chlorophenyl)-5,7-dimethyl-1-(p-toluenesulfonyl)indole-2-yl]-N'-(2-isopropyl-6-methylphenyl)urea (compound 121)
 Yield 62.1%.
 NMR (δ, ppm; DMSO-d$_6$) 1.06 (d, 6H), 2.03 (s, 3H), 2.23 (s, 3H), 2.30 (s, 3H), 2.60 (s, 3H), 3.08 (m, 1H), 6.55 (s, 1H), 6.90–7.60 (m, 12H), 7.83 (s, 1H), 8.55 (s, 1H).

Example 122

N-[3-(2-Chlorophenyl)-5,7-dimethyl-1-(p-toluenesulfonyl)indole-2-yl]-N'-(2,4-difluorophenyl)urea (compound 122)
 Yield 59.0%, m.p. 240°–241° C.
 NMR (δ, ppm; CDCl$_3$) 2.27 (s, 3H), 2.35 (s, 3H), 2.76 (s, 3H), 6.71 (s, 1H), 6.75–6.88 (m, 1H), 7.02–7.47 (m, 12H), 7.80–7.90 (m, 1H).

Example 123

N-[3-(2-Chlorophenyl)-5,7-dimethyl-1-methylindole-2-yl]-N'-(2-isopropyl-6-methylphenyl)urea (compound 123)
 Yield 21.5%, m.p. 263°–264° C.
 NMR (δ, ppm; DMSO-$_6$) 1.10 (d, 6H), 2.16 (s, 3H), 2.27 (s, 3H), 2.72 (s, 3H), 3.10 (m, 1H), 3.90 (s, 3H), 6.72 (s, 1H), 6.82 (s, 1H), 7.02–7.18 (m, 3H), 7.35–7.45 (m, 3H), 7.55–7.63 (m, 1H), 7.75 (broad, 1H), 8.30 (s, 1H).

Example 124

N-[3-(2-Chlorophenyl)-5,7-dimethyl-1-methylindole-2-yl]-N'-(2,4-difluorophenyl)urea (compound 124)
 Yield 59.0%, m.p. 240°–241° C.
 NMR (δ, ppm; CDCl$_3$) 2.35 (s, 3H), 2.78 (s, 3H), 3.97 (s, 3H), 6.62 (s, 2H), 6.72–6.82 (m, 1H), 6.88 (s, 1H), 7.06 (s, 1H), 7.26–7.35 (m, 2H), 7.41–7.50 (m, 2H), 7.67–7.78 (m, 1H).

Example 125

N-[3-(2-Chlorophenyl)-5,7-dimethyl-1-methylindole-2-yl]-N'-(4-dimethylaminophenyl)urea (compound 125)
 Yield 44.5%, m.p. 255°–256° C.
 NMR (δ, ppm DMSO-d$_6$) 2.29 (s, 3H), 2.73 (s, 3H), 2.82 (s, 6H), 3.85 (s, 3H), 6.66 (d, 2H), 6.73 (S, 1H), 7.20 (d, 2H), 7.31–7.42 (m, 3H), 7.57 (d, 1H), 7.98 (s, 1H), 8.40 (s, 1H).

Reference Example 1

3-(2-Chlorophenyl)-5-fluorobenzofuran-2-carboxylic acid
1) 4-Fluorophenyl 2-chlorobenzoate (compound A)
 To a stirred solution of 25 g of 4fluorophenol in 40 cc of pyridine and 30 cc of toluene was added dropwise 40.9 g of 2-chlorobenzoylchloride at room temperature. And the resulting mixture was stirred at room temperature for 16 hours. Ice water was added to the reaction mixture and extracted with ethyl acetate. The ethylacetate layer was washed 4 times with 1N HCl, dried over magnesium sulfate. The solvent was distilled off and the crude product thus obtained was recrystallized from hexane to obtain 49.1 g of compound A. Yield: 87.8%.
2) 2-Chloro-5'-fluoro-2'-hydroxybenzophenone (compound B)
 To a stirred solution of 2.5 g of compound A was added in small portions 1.47 g of powdered aluminum chloride at 130° C. and stirring was continued for another 1 hour. After cooling 1N HCl and chloroform was added to the reaction mixture and the organic layer was separated. The aqueous layer was extracted with chloroform. The combined organic layer was dried over magnesium sulfate and distilled to remove the solvent. The crude product thus obtained was crystallized from hexane to obtain 1.41 g of compound B. Yield: 56.3%.
3) Ethyl 6-(2-Chlorobenzoyl)-2,4-dimethylphenoxyacetate (compound C)
 To a stirred mixture of 1.0 g of compound B and 1.1 g of potassium carbonate in 10 cc of dimethylformamide was added dropwise 0.53 cc of ethyl bromoacetate at room temperature. After the resulting mixture was stirred at room temperature for 16 hours. The insoluble material was filtered off. To the filtrate was added water and ethylacetate and the aqueous layer was extracted with ethyl acetate. The combined organic layer was washed three times with a saturated aqueous sodium chloride solution and dried over magnesium sulfate. The solvent was distilled off and the crude product thus obtained was purified by a silica gel column chromatography (eluent: ethyl acetate/hexane=1/4) to obtain 1.06 g of compound C. Yield: 78.7%.
4) Ethyl 3-(2-chlorophenyl)-5-fluorobenzofuran-2-carboxylate (compound D)
 To a stirred solution of sodium ethoxide prepared from 0.23 g of Na and 10 cc of ethanol was added dropwise 3.4 g of compound C in 10 cc of tetrahydrofuran at room temperature. And the resulting mixture was heated under reflux for 30 minutes. After cooling, the reaction mixture was poured into ice water and acidified with 1N HCl, which was then extracted three times with chloroform. The combined organic layer was washed with a saturated aqueous sodium chloride solution and dried over magnesium sulfate. The solvent was distilled off and the crude product thus obtained was purified by a silica gel column chromatography (eluent: ethyl acetate/hexane=1/6) to obtain 0.89 g of compound D. Yield: 27.9%.

5) 3-(2-Chlorophenyl)-5-fluorobenzofuran-2-carboxylic acid

A mixture of 3.69 g of compound D and 1.95 g of powdered potassium hydroxide in 30 cc of ethanol and 4 cc of water was heated under reflux for 6 hours. After cooling, ice water was added and the resulting mixture was washed with hexane. The aqueous layer was acidified with 1N HCl, and extracted with chloroform, which was then dried over magnesium sulfate. The solvent was distilled off to obtain 3.14 g of 3-(2 -chlorophenyl)-5-fluorobenzofuran-2-carboxylic acid. Yield: 93.3%.

The following compounds were obtained in the same manner as in Reference Example 1:
(1) 5-chloro-(2-chlorophenyl)benzofuran-2-carboxylic acid,
(2) 3-(2-chlorophenyl)-5-methylbenzofuran-2-carboxylic acid,
3) 3-(2-Chlorophenyl)-5-ethylbenzofuran-2-carboxylic acid,
(4) 3-(2-chlorophenyl)-5-n-hexylbenzofuran-2-carboxylic acid,
(5) 3-(2-chlorophenyl)-5-methoxybenzofuran-2-carboxylic acid,
(6) 3-(2-chlorophenyl)-5-dimethylaminomethylbenzofuran-2-carboxylic acid,
(7) 3-(2-chlorophenyl)-5-(1-pyrrolidinomethyl)benzofuran-2-carboxylic acid,
(8) 3-(2-chlorophenyl)-5-(1-morpholinomethyl)benzofuran-2-carboxylic acid,
(9) 3-(2-chlorophenyl)-(4-methyl-1-piperazinomethyl)benzofuran- 2-carboxylic acid,
(10) 3-(2-chlorophenyl)-5,6-dimethylbenzofuran-2-carboxylic acid,
(11) 3-(2-chlorophenyl)-5,7-dimethylbenzofuran-2-carboxylic acid,
(12) 3-(2-chlorophenyl)-6,7-dihydro-5H-cyclopenta[f]benzofuran-2-carboxylic acid,
(13) 5-chloro-3-(2-fluorophenyl)benzofuran-2-carboxylic acid,
(14) 5-chloro-3-(2-methylphenyl)benzofuran-2-carboxylic acid,
(15) 5-chloro-3-(2-methylthiophenyl)benzofuran-2-carboxylic acid.

Reference Example 2

5-Methyl-3-phenylbenzofuran-2-carboxylic acid
1) Ethyl α-(4-Methylphenyl)benzoylacetate (compound E)

A mixture of 7.66 g of ethyl α -diazobenzoylacetate, 3.8 g of p-cresol and 150 mg of rhodium(II) acetate in 40 cc of carbon tetrachloride was stirred at a temperature of 40–50° C. for 2 hours. After cooling, the insoluble materials were filtered off and the solvent was distilled off. The crude product thus obtained was purified by a silica gel column chromatography (eluent: chloroform/hexane=1/2) to obtain 2.59 g of compound E. Yield: 24.7%.

2) 5-Methyl-3-phenylbenzofuran-2-carboxylic acid

A mixture of 1.79 g compound E in 5 cc of concentrated sulfuric acid was stirred under ice-cooling for 1 hour. The reaction mixture was poured into ice water and was extracted with chloroform, which was then washed with water, a saturated aqueous sodium bicarbonate solution and a saturated aqueous sodium chloride solution successively, and dried over magnesium sulfate. The solvent was distilled off and the residue was crystallized from hexane to obtain 1.30 g of ethyl 5-methyl-3-phenylbenzofuran-2-carboxylate (compound F). Yield: 77.3% or less. 3-Phenyl-5-methylbenzofuran-2-carboxylic acid was obtained in the same manner as in the step 5 of Reference Example 1 except for using compound F.

Reference Example 3

5-Chloro-3-(2-chlorophenyl)-1-benzothiophene-2-carboxylic acid
1) 5-Chloro-2-methylthio-2'-chlorobenzophenone (compound G)

To 57.9 g of aluminum chloride was added dropwise 54.7 ml of 2-chlorobenzoyl chloride at room temperature, and the resulting mixture was stirred at room temperature for 30 minutes. Then, 24.0 g of 4-chlorophenylmethyl sulfide was added dropwise at room temperature and stirring was continued for 16 hours. The reaction mixture was poured into ice water and extracted with ether, which was then washed with water and an aqueous sodium bicarbonate solution. The extract was dried over magnesium sulfate and distilled to remove the solvent. The crude product thus obtained was purified by a silica gel column chromatography (eluent: ethyl acetate/hexane=1/19) to obtain 13.1 g of 5 -chloro-2-methylthio-2'-chlorobenzophenone (compound G). Yield: 31.5%.

2) 5-Chloro-3-(2-chlorophenyl)-1-benzothiophen-2 -carboxylic acid

A mixture of 4.9 g of compound G and 7.8 g of chloroacetic acid was stirred at 120° C. for 10 hours. After cooling, water was added to the reaction mixture and the precipitate formed was collected by filtration. The precipitate was dissolved in ethyl acetate and washed with water. The solution was dried over magnesium sulfate and distilled to remove the solvent. The crude product thus obtained was washed with ether to obtain 4.45 g of 5-chloro-3-(2-chlorophenyl)-1 -benzothiophen-2-carboxylic acid. Yield: 83.3%.

The following compounds were obtained in the same manner as in Reference Example 3:
(1) 3-(2-chlorophenyl)-5-methyl-1-benzothiophene--carboxylic acid,
(2) 3-(2-Chlorophenyl)-5-isopropyl-1 -benzothiophene-2-carboxylic acid,
(3) 3-(2-chlorophenyl)-5,6-dimethyl-1 -benzothiophene-2-carboxylic acid,
(4) 3-(2-chlorophenyl)-6,7-dihydro-5H-cyclopenta[f][1] benzothiophene-2-carboxylic acid,
(5) 3-(2-chlorophenyl)-5,6,7,8-tetrahydronaphtho[2,3-b] thiophene-2-carboxylic acid,
(6) 3-(2,4-dichlorophenyl)-5-nitro-1-benzothiophene-2-carboxylic acid,
(7) 3-(2-chlorophenyl)-5,6-dimethoxy-1 -benzothiophene-2-carboxylic acid,
(8) 3-(2,4-dichlorophenyl)-6,7-dihydro-5H-cyclopenta[f][1] benzothiophene-2-carboxylic acid,
(9) 3-(2-methylphenyl)-6,7-dihydro-5H-cyclopenta[f][1] benzothiophene-2-carboxylic acid,
(10) 3-(2-trifluoromethylphenyl)-6,7-dihydro-5H-cyclopenta[f][1]benzothiophene-2-carboxylic acid,
(11) 3-(2-methylphenyl)-5,6,7,8-tetrahydronaphtho[2,3-b] thiophene-2-carboxylic acid.

Reference Example 4

3-Phenyl-1-(p-toluenesulfonylindole)-2-carboxylic acid
2-(p-Toluenesulfonylamino)benzophenone (compound H)

To a stirred solution of 15.0 g of 2-aminobenzophenone in 7.5 cc of pyridine was added 14.5 g of p-toluenesulfonyl chloride under ice-cooling. And the resulting mixture was stirred at room temperature for 16 hours. 2N HCl was added to the reaction mixture and extracted with ethyl acetate. The extract was washed with water and dried over magnesium sulfate. The solvent was distilled off and the crude crystals thus obtained were recrystallized from isopropanol to obtain 22.0 g of compound H. Yield: 82.4%.

t-Butyl N-(2-benzoylphenyl)-N-(p-toluenesulfonyl)aminoacetate (compound I)

To a stirred solution of 5.0 g of compound H in 10 cc of dimethylformamide was added 0.56 g of 63% sodium hydride in 5 cc of dimethylformamide under ice-cooling and the mixture was stirred for 30 minutes. Then, 2.3 cc of t-butyl bromoacetate was added dropwise at the same temperature and stirring was continued for 16 hours. Water was added to the reaction mixture and the desired compound was extracted with ethyl acetate. The extract was washed with water and dried over magnesium sulfate. The solvent was distilled off and the crude product thus obtained was washed with hexane to obtain 6.31 g of compound I. Yield: 95.4%.

3) t-Butyl 3-phenyl-1-(p-toluenesulfonyl)indole-2-carboxylate (compound J)

To a stirred solution of 2.30 g of compound I in 175 cc of methanol was added 0.39 g of sodium methoxide at room temperature and the mixture was stirred for 16 hours. The methanol was distilled off and to the residue was added water, followed by extraction with ethyl acetate. The extract was dried over magnesium sulfate and distilled to remove the solvent. The resulting crude product was dissolved in 50 cc of benzene, followed by adding dropwise thereto 1.41 cc of pyridine and then 0.52 g of thionyl chloride at room temperature, and the resulting mixture was stirred at room temperature for 1 hour. Water was added to the reaction mixture and extracted with ethyl acetate. The extract was dried over magnesium sulfate and distilled to remove the solvent. the crude product thus obtained was purified by a silica gel column chromatography (eluent: ethyl acetate/hexane=1/4) to obtain 2.55 g of compound J. Yield: 80.2%.

3-Phenyl-1-(p-toluenesulfonyl)indole-2-carboxylic acid

To a stirred solution of 2.55 g of compound J in 10 cc of methylene chloride was added 2.20 g of trichloroacetic acid under ice-cooling and the mixture was stirred for 16 hours. Water was added to the reaction mixture, the desired compound was extracted with ethyl acetate. The extract was dried over magnesium sulfate and distilled to remove the solvent. The crude product thus obtained was purified by a silica gel column chromatography (eluent: ethyl acetate/hexane=3/7) to obtain 2.10 g of 3-phenyl-1-(p-toluenesulfonyl)indole-2-carboxylic acid. Yield: 94.1%.

5,7-Dimethyl-3-phenyl-1-(p-toluenesulfonyl)indole-2-carboxylic acid was obtained in the same manner as in Reference Example 4.

Reference Example 5

3-(2-Chlorophenyl)-1,5,7-trimethylindole-2-carboxylic acid

Methyl 1-(2-chlorobenzoyl)-3-(2-chlorophenyl)-5,7-dimethylindole-2-carboxylate (compound K) was obtained in the same manner as for compounds I and J in Reference Example 4. In 20 cc of methanol was dissolved 0.96 g of compound K, followed by adding thereto 4.2 cc of 2N sodium hydroxide, and the resulting mixture was heated under reflux for 2 hours. After cooling, the mixture was acidified with 2N HCl, followed by extraction with ethyl acetate. The extract was dried over magnesium sulfate and distilled to remove the solvent. The resulting crude product was dissolved in 2 cc of dimethylformamide, and 0.26 g of 63% sodium hydride in 1.5 cc of dimethylformamide was added at room temperature. The resulting mixture was stirred at room temperature for 30 minutes, and then 0.4 cc of methyl iodide was added dropwise and stirred for 2 hours. Water was added to the reaction mixture, followed by extraction with ethyl acetate. The extract was dried over magnesium sulfate and distilled to remove the solvent. The crude product thus obtained was washed with hexane to obtain 0.41 g of methyl 3-(2-chlorophenyl)-1,5,7-trimethylindole-2-carboxylate (compound L).

3-(2-Chlorophenyl)-1,5,7-trimethylindole-2-carboxylic acid was obtained in the same manner as in Reference Example 1 except for using compound L.

The compounds of the present invention are administered as a propylactic and therapeutic agent for hypercholesterolemia and atherosclerosis orally or parenterally (intramuscularly, subcutaneously or intravenously). They are administered to human beings preferably orally. Since the compounds of the present invention are applicable in themselves as ACAT inhibitors, they are contained in compositions as active ingredients usually in an amount of 0.01 to 100% by weight. Although the dose of the compounds is varied depending on the condition of a disease, age, sex, body weight, administration route, etc., the dose for an adult is usually 0.1 to 1000 mg per day.

When the compound of the present invention is formulated into a pharmaceutical form, it is prepared into powder, granules, tablets, dragées, capsules, pills, a suspension, solution, emulsion, ampule, injection, isotonic solution or the like by a conventional preparation method. When an oral solid pharmaceutical is prepared, an excipient and optionally a binder, wetting agent, disintegrator, surfactant, lubricant, dispersant, taste-improver, odor-improver, etc. are added to the active ingredient, and the resulting mixture is made into tablets, coated tablets, granules, capsules or the like by a conventional method. The excipient includes, for example, lactose, glucose, sorbitol, corn starch and mannitol. The binder includes, for example, poly(vinyl alcohol)s, poly(vinyl ether)s, ethyl cellulose, gum arabic, gelatin, hydroxypropyl cellulose and poly(vinylpyrrolidone)s. The disintegrator includes, for example, calcium carbonate, calcium citrate, dextrin, starch and gelatin powder. The lubricant includes, for example, magnesium stearate, talc and poly(ethylene glycol)s. The odor-improver includes, for example, cocoa powder, menthol, and peppermint oil. The tablets and the granules may be properly coated with a frosting, gelatin or the like if necessary. When an injection is prepared, a pH adjustor, buffer, surfactant, solubilizer, solvent, stabilizer, preservative, etc. are added to the active ingredient if necessary, and the resulting mixture is made into a subcutaneous, intramuscular or intravenous injection by a conventional method.

Formulation examples are described below but they are not intended in any way to limit the scope of the invention. In the formulation examples, parts are all by weight.

Formulation Example 1

A powder was prepared by mixing uniformly and pulverizing or granulating finely the following ingredients:

| | |
|---|---|
| Each compound of the invention | 10 parts |
| Magnesium stearate | 10 parts |

| | |
|---|---|
| -continued | |
| Lactose | 80 parts |

Formulation Example 2

Granules were prepared by kneading together uniformly, grinding, and granulating the following ingredients, followed by sieving:

| | |
|---|---|
| Each compound of the invention | 50 parts |
| Starch | 10 parts |
| Lactose | 15 parts |
| Ethyl cellulose | 20 parts |
| Poly(vinyl alcohol) | 5 parts |
| Water | 30 parts |

Formulation Example 3

Tablets with a diameter of 10 mm were prepared by mixing 99 parts of the granules obtained in Formulation Example 2 with 1 part of calcium stearate, and compression-molding the resulting mixture.

Formulation Example 4

Granules were prepared in the same manner as in Formulation Example 2 except for using the following ingredients:

| | |
|---|---|
| Each compound of the invention | 95 parts |
| Poly(vinyl alcohol) | 5 parts |
| Water | 30 parts |

To 90 parts of the granules obtained was added 10 parts of crystalline cellulose, and the resulting mixture was compression-molded into tablets with a diameter of 8 mm. Then, the tablets were made into dragée by the use of suitable amounts of a mixed suspension of syrup, gelatin and precipitated calcium carbonate and a coloring agent.

Formulation Example 5

An injection was prepared by mixing by heating, and then sterilizing the following ingredients:

| | |
|---|---|
| Each compound of the invention | 0.5 part |
| Nonionic surfactant | 2.5 parts |
| Physiological saline | 97 parts |

Formulation Example 6

Capsules were prepared by packing the powder obtained in Formulation Example 1 into commercially available capsular containers.

Next, test examples are described below for proving the effectiveness of the present invention.

Test Example 1

Inhibitory activity on acyl-CoA:cholesterol Oacyltransferase (ACAT)

The enzyme used in the test was prepared according to the method of Heider et al. [J. Lipid, Res. 24, 1127 (1983)]. The intestinal mucosa of a white rabbit was homogenized and microsomal fraction was obtained by stepwise centrifugation. The microsomal fraction was suspended in 0,154M phosphate buffer (pH 0 7.4) and stored at −80° C. until use.

ACAT activity was determined by a modification of the method of Helgerud et al. [J. Lipid Res. 22, 271 (1981)] by measuring radioactivity incorporated into cholesterol esters from [1–14C]oleyl-CoA, as an indication. As to the ACAT-inhibiting activity of each compound to be tested, the inhibition rate was calculated by the following equation. The results obtained are shown in Table 2.

$$\text{Inhibition rate (\%)} = \frac{\left[\begin{array}{c}\text{ACAT activity of}\\\text{control group which}\\\text{was given solvent}\end{array}\right] - \left[\begin{array}{c}\text{ACAT activity of}\\\text{group treated with}\\\text{compound to be tested}\end{array}\right]}{\left[\begin{array}{c}\text{ACAT activity of control}\\\text{group which was given solvent}\end{array}\right]} \times 100$$

| Compound | (Inhibition rate %) | |
|---|---|---|
| No. | 1 | 0.01 μM |
| 1 | | 49.8 |
| 2 | | 58.3 |
| 4 | 77.9 | |
| 5 | 98.5 | 15.4 |
| 7 | 99.1 | 37.2 |
| 8 | 97.4 | 24.9 |
| 12 | 99.4 | 82.9 |
| 13 | 99.4 | 84.9 |
| 15 | 99.4 | 76.8 |
| 19 | | 71.3 |
| 22 | | 69.3 |
| 25 | | 73.3 |
| 26 | | 41.2 |
| 27 | | 63.5 |
| 30 | | 58.4 |
| 36 | 98.9 | 37.6 |
| 37 | 99.5 | 74.7 |
| 38 | 99.5 | 77.2 |
| 39 | 99.4 | 70.9 |
| 43 | 99.5 | 52.1 |
| 45 | 94.0 | |
| 46 | 92.7 | |
| 47 | 93.0 | |
| 48 | 95.6 | 6.8 |
| 49 | 99.1 | 51.9 |
| 53 | | 43.7 |
| 55 | | 32.1 |
| 58 | | 69.2 |
| 60 | | 82.6 |
| 61 | | 65.6 |
| 62 | | 91.6 |
| 63 | | 72.1 |
| 65 | 99.1 | 56.5 |
| 72 | | 60.6 |
| 76 | | 71.0 |
| 77 | | 51.7 |
| 80 | | 69.9 |
| 81 | | 41.4 |
| 82 | | 67.0 |
| 83 | | 81.3 |
| 84 | | 78.6 |
| 87 | | 60.4 |
| 88 | | 85.8 |
| 89 | | 44.4 |
| 90 | | 75.4 |
| 91 | | 65.0 |

-continued

| Compound No. | (Inhibition rate %) | |
|---|---|---|
| | 1 | 0.01 μM |
| 92 | | 81.7 |
| 93 | | 69.7 |
| 94 | | 76.7 |
| 95 | | 66.4 |
| 96 | | 80.7 |
| 98 | | 66.0 |
| 99 | | 90.1 |
| 100 | | 18.4 |
| 102 | | 43.3 |
| 107 | | 36.2 |
| 109 | | 80.1 |
| 111 | | 69.2 |
| 113 | | 43.5 |
| 119 | | 79.5 |
| 120 | 60.4 | |
| 121 | 85.8 | |
| 122 | 75.4 | |
| 124 | 81.7 | |

Test Example 2

Serum cholesterol lowering activity in hamsters fed on a high-cholesterol diet

Male Syrian hamsters of 10-week-old were divided into three groups. The first group (normal group) was fed an ordinary diet for 4 days. The second group (control group) was fed a high cholesterol diet (containing 0.5% cholesterol and 8.0% coconut oil for 4 days. The third group (treated group) was fed a high cholesterol diet and was treated with a compound for 4 days. Simultaneously with the beginning of the above feeding, the compound suspended in a 0.5% carboxymethyl cellulose solution was administered to the treated group, in a dose of 30 mg (in terms of the compound) per kg of body weight per day for 4 days. A 0.5% carboxymethyl cellulose solution was also administered to the normal group and the control group in the same manner as above. After 24 hours of the last administration, blood was collected and the cholesterol concentration in serum was measured by an enzymatic method. The reduction rate of the total serum cholesterol concentration was calculated from values obtained for the three groups by the following equation. The results obtained are shown in Table 3.

$$\text{Cholesterol reduction rate (\%)} = \frac{(A) - (B)}{(A) - (C)} \times 100$$

wherein
A: the serum cholesterol concentration of the control group.
B: the serum cholesterol concentration of the compound treated group.
C: the serum cholesterol concentration of the normal group.

TABLE 3

| Compound No. | Reduction rate (%) |
|---|---|
| 12 | 55.0 |
| 37 | 59.3 |
| 80 | 85.9 |

TABLE 3-continued

| Compound No. | Reduction rate (%) |
|---|---|
| 109 | 71.5 |

Test Example 3

Inhibitory effect on cholesterol esterification in macrophages

The test was carried out by a modification of the method of Goldstein et al. [Pro. Nat. Acad. Sci. USA 71, 4288 (1974)]. J774 A.1 cells, the mouse macropharge-like cell line, were suspended in Dulbecco's modified Eagle's medium (DMEM) containing 10% fetal calf serum (FCS), in a proportion of $3\times10^5$ cells per 2 ml and were seeded into in 6-well plates. The cells were cultured under a humidified atmosphere of 95% air/5% $CO_2$ at 37° C. for 24 hours. The medium was replaced by 1 ml of DMEM containing 10% of FCS and 50 μg/ml of acetylated human low density lipoprotein (AcLDL), followed by culturing for 16 hours. Five microliters each compound was dissolved in dimethyl sulfoxide and solution was added to the medium, followed by culturing for another 2 hours. Then, [14C]oleate ($2\times10^6$ dpm/well) bovine serum albumin complex was added in the medium. After 2 hours of culture cells were collected and the cholesterol-esterifying activity was determined by measuring radioactivity incorporated into cholesterol esters in the cells. The recovery of the cholesterol esters was determined by the addition of [3H]cholesteryl oleate, and the esterifying activity was corrected using the recovery. As to the inhibitory activity on cholesterol esterification of the compound to be tested, the inhibition rate was calculated by the following equation. The results obtained are shown in Table 4.

$$\text{Inhibition rate of cholesterol esterification (\%)} = \frac{(B) - (A)}{(B)} \times 100$$

wherein
A: the cholesterol-esterifying activity of AcLDL-loaded cells to which the compound to be tested was-added.
B: the cholesterol-esterifying activity of AcLDL-loaded cells to which dimethyl sulfoxide was added.

TABLE 4

| Compound No. | 1 | 0.1 μM | Inhibition rate (%) |
|---|---|---|---|
| 12 | 99.5 | 93.0 | |
| 80 | 96.9 | 85.3 | |

Effect of the Invention

The N-heteroaryl-N'-phenylurea derivatives of the present invention have ACAT-inhibitory activity and are useful as a prophylactic and therapeutic agent for hypercholesterolemia, atherosclerosis and various diseases caused by them.

What is claimed is:
1. An N-heteroaryl-N'-phenylurea derivative represented by the general formula (I):

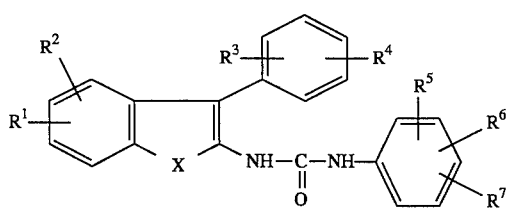

wherein $R^1$ and $R^2$, which may be the same or different, are hydrogen atoms; halogen atoms; unsubstituted $C_1$–$C_{10}$ alkyl groups; substituted $C_1$–$C_6$ alkyl groups having a $C_2$–$C_8$-dialkylamino group as the substituent; substituted $C_1$–$C_6$ alkyl groups having as the substituent a saturated cyclic amino group which may have a heteroatom in the ring; $C_1$–$C_6$ alkoxy groups; or nitro groups, $R^1$ and $R^2$ being able to be taken together to represent a $C_3$–$C_6$ alkylene group, $R^3$ and $R^4$, which may be the same or different, are hydrogen atoms, halogen atoms, $C_1$–$C_6$ alkyl groups, $C_1$–$C_6$ haloalkyl groups, $C_1$–$C_6$ alkoxy groups or $C_1$–$C_6$ alkylthio groups, $R^5$, $R^6$ and $R^7$, which may be the same or different, are hydrogen atoms, halogen atoms, $C_1$–$C_8$ alkyl groups, $C_1$–$C_6$ haloalkyl groups, $C_3$–$C_7$ alkenyl groups, $C_1$–$C_6$ alkoxy groups, $C_1$–$C_6$ alkylthio groups or $C_2$–$C_8$-dialkylamino groups, and X is —S— or a pharmacologically acceptable salt thereof.

2. An N-heteroaryl-N'-phenylurea derivatives according to claim 1, wherein $R^1$ is a halogen atom or a $C_1$–$C_{10}$ alkyl group, $R^2$ is a hydrogen atom or a $C_1$–$C_6$ alkyl group, $R^1$ and $R^2$ being able to be taken together to represent a $C_3$–$C_6$ alkylene group, $R^3$ is a halogen atom, a $C_1$–$C_4$ alkyl group, a $C_1$–$C_4$ alkylthio group or trifluoromethyl group, $R^4$ is a hydrogen atom or a halogen atom, $R^5$ and $R^6$ which may be the same or different, are halogen atoms or $C_1$–$C_4$ alkyl groups, and R7 is a hydrogen atom or a halogen atom.

3. An N-heteroaryl-N'-phenylurea derivative according to claim 1, wherein $R^1$ is a chlorine atom or a $C_1$–$C_8$ alkyl group, $R^2$ is a halogen atom or a $C_1$–$C_3$ alkyl group, $R^1$ and $R^2$ being able to be taken together to represent a $C_3$–$C_4$ alkylene group, $R^3$ is a halogen atom, a $C_1$–$C_4$ alkyl group or a $C_1$–$C_4$ alkylthio group, $R^4$ is a hydrogen atom, $R^5$ and $R^6$ which may be the same, are halogen atoms or $C_1$–$C_4$ alkyl groups, and $R^7$ is a hydrogen atom.

4. A pharmaceutical composition for inhibiting acyl-CoA:cholesterol O-acrylransferase comprising as active ingredient a compound represented by the general formula (I):

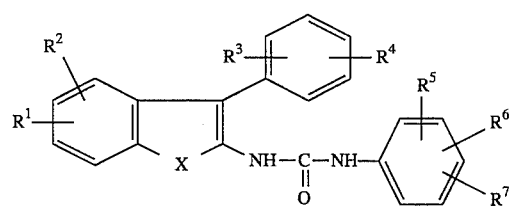

wherein $R^1$ and $R^2$, which may be the same or different, are hydrogen atoms; halogen atoms; unsubstituted $C_1$–$C_{10}$ alkyl groups; substituted $C_1$–$C_6$ alkyl groups having a $C_2$–$C_8$-dialkylamino group as the substituent; substituted $C_1$–$C_6$ alkyl groups having as the substituent a saturated cyclic amino group which may have a heteroatom in the ring; $C_1$–$C_6$ alkoxy groups; or nitro groups, $R^1$ and $R^2$ being able to be taken together to represent a $C_3$–$C_6$ alkylene group, $R^3$ and $R^4$, which may be the same or different, are hydrogen atoms, halogen atoms, $C_1$–$C_6$ alkyl groups, $C_1$–$C_6$ haloalkyl groups, $C_1$–$C_6$ alkoxy groups or $C_1$–$C_6$ alkylthio groups, $R^5$, $R^6$ and $R^7$, which may be the same or different, are hydrogen atoms, halogen atoms, $C_1$–$C_8$ alkyl groups, $C_1$–$C_6$ haloalkyl groups, $C_3$–$C_7$ alkenyl groups, $C_1$–$C_6$ alkoxy groups, $C_1$–$C_6$ alkylthio groups or $C_2$–$C_8$-dialkylamino groups, and X is —S— or a pharmacologically acceptable salt thereof, and a pharmacologically acceptable carrier.

5. A pharmaceutical composition for inhibiting acyl-CoA:chlesterol O-acyltransferase according to claim 4, wherein $R^1$ is a halogen atom or a $C_1$–$C_{10}$ alkyl group, $R^2$ is a hydrogen atom or a $C_1$–$C_6$ alkyl group, $R^1$ and $R^2$ being able to be taken together to represent a $C_3$–$C_6$ alkylene group, Rhu is a halogen atom, a $C_1$–$C_4$ alkyl group, a $C_1$–$C_4$ alkylthio group or trifluoromethyl group, $R^4$ is a hydrogen atom or a halogen atom, $R^5$ and $R^6$ which may be the same or different, are halogen atoms or $C_1$–$C_4$ alkyl groups, and $R^7$ is a hydrogen atom or a halogen atom.

6. A pharmaceutical composition for inhibiting acyl-CoA:cholesterol O-acyltransferase according to claim 4, wherein $R^1$ is a chlorine atom or a $C_1$–$C_8$ alkyl group, $R^2$ is a hydrogen atom or a $C_1$–$C_3$ alkyl group, $R^1$ and $R^2$ being able to be taken together to represent a $C_3$–$C_4$ alkylene group, $R^3$ is a halogen atom, a $C_1$–$C_4$ alkyl group or a $C_1$–$C_4$ alkylthio group, $R^4$ is a hydrogen atom, $R^5$ and $R^6$ which may be the same, are halogen atoms or $C_1$–$C_4$ alkyl groups, and $R^7$ is a hydrogen atom.

* * * * *